US010258456B2

(12) United States Patent
Morita et al.

(10) Patent No.: US 10,258,456 B2
(45) Date of Patent: Apr. 16, 2019

(54) CELL-CONTAINING SHEET

(71) Applicants: National University Corporation Tokyo Medical and Dental University, Tokyo (JP); DAI NIPPON PRINTING CO., LTD., Tokyo (JP)

(72) Inventors: Ikuo Morita, Tokyo (JP); Akiko Kobayashi, Tokyo (JP); Hideshi Hattori, Tokyo (JP); Masatoshi Kuroda, Tokyo (JP)

(73) Assignees: National University Corporation Tokyo Medical and Dental University, Tokyo (JP); DAI NIPPON PRINTING CO., LTD., Tokyo (JP)

( * ) Notice: Subject to any disclaimer, the term of this patent is extended or adjusted under 35 U.S.C. 154(b) by 33 days.

(21) Appl. No.: 15/214,756

(22) Filed: Jul. 20, 2016

(65) Prior Publication Data

US 2016/0324623 A1 Nov. 10, 2016

Related U.S. Application Data

(62) Division of application No. 11/455,112, filed on Jun. 19, 2006.

(30) Foreign Application Priority Data

Jun. 17, 2005 (JP) .................................. 2005-178394

(51) Int. Cl.
| | | |
|---|---|---|
| A61F 2/02 | (2006.01) |
| A61L 27/36 | (2006.01) |
| A61L 27/38 | (2006.01) |
| A61K 35/12 | (2015.01) |
| C12N 5/00 | (2006.01) |
| C12N 5/071 | (2010.01) |
| A61L 27/58 | (2006.01) |
| B82Y 30/00 | (2011.01) |

(52) U.S. Cl.
CPC ............ *A61F 2/02* (2013.01); *A61L 27/3604* (2013.01); *A61L 27/3804* (2013.01); *A61L 27/3808* (2013.01); *A61L 27/3843* (2013.01); *A61L 27/58* (2013.01); *B82Y 30/00* (2013.01); *C12N 5/0068* (2013.01); *C12N 5/069* (2013.01); *A61F 2210/0076* (2013.01); *A61F 2240/001* (2013.01); *A61F 2250/0067* (2013.01); *A61K 35/12* (2013.01); *A61L 2430/12* (2013.01); *A61L 2430/34* (2013.01); *C12N 2533/92* (2013.01); *C12N 2535/10* (2013.01)

(58) Field of Classification Search
CPC ................ A61F 2/02; A61F 2210/0076; A61F 2240/001; A61F 2250/0067; A61L 27/3808; A61L 27/3604; A61L 27/3804; A61L 27/58; A61L 27/3843; A61L 2430/12; A61L 2430/34; C12N 5/069; C12N 5/0068; C12N 2535/10; C12N 2533/92; B82Y 30/00; A61K 35/12
See application file for complete search history.

(56) References Cited

U.S. PATENT DOCUMENTS

| | | | |
|---|---|---|---|
| 5,723,010 | A | 3/1998 | Yui et al. |
| 2005/0027356 | A1 | 2/2005 | Fishman et al. |
| 2005/0214345 | A1 | 9/2005 | Leng et al. |
| 2006/0002900 | A1 | 1/2006 | Binder et al. |
| 2007/0122901 | A1 | 5/2007 | Morita et al. |

FOREIGN PATENT DOCUMENTS

| | | |
|---|---|---|
| EP | 0 734 736 A1 | 10/1996 |
| JP | 3-007576 A | 1/1991 |
| JP | 5-176753 A | 7/1993 |
| JP | 08-266613 A | 10/1996 |
| JP | 2001-161353 A | 6/2001 |
| JP | 2003-038170 A | 2/2003 |
| JP | 2003-532466 A | 11/2003 |
| JP | 2004-024852 A | 1/2004 |
| WO | 01/80760 A1 | 11/2001 |

OTHER PUBLICATIONS

MacNeill et al. Toward a new blood vessel. Vascular Medicine 2002; 7: 241-246. (Year: 2002).*
Japanese Office Action dated Feb. 8, 2011, issued in corresponding Japanese Application No. 2005-178394.
Hynda K. Kleinman, et al.; "Matrigel: Basement Membrane Matrix with Biological Activity"; Seminars in Cancer Biology; 2005; vol. 15; pp. 378-386.
Japanese Office Action dated Jul. 12, 2011 issued in Japanese Patent Application No. 2005-178394.
Journal of Clinical and Experimental Medicine (Igaku No Ayumi), vol. 211, No. 7, Nov. 13, 2004, p. 769-771.
Success in formation of capillary network through the applied use of printing technology, Medical Technology, vol. 33, No. 5, (May 2005), pp. 443-444.
An English language abstract of Japanese International Application No. 2005/038011.
Amemiya et al. Human oral epithelial and periodontal ligament cells sheets cultured on human amniotic membrane for oral reconstruction. J. Oral Tissue Engin. 2004:1(1):89-96.

(Continued)

*Primary Examiner* — Taeyoon Kim
(74) *Attorney, Agent, or Firm* — Sughrue Mion, PLLC

(57) ABSTRACT

In accordance with the present invention, an implant in which cells are arranged in a fine pattern that is available for immediate implantation and that does not need to be removed after implantation is provided. The present invention relates to a cell-containing sheet, which comprises cells and a support comprising a bioabsorbable material, in which the support has a cell adhesion protein-containing layer on the surface thereof and the cells form a pattern on the support.

6 Claims, 14 Drawing Sheets
(5 of 14 Drawing Sheet(s) Filed in Color)

(56) References Cited

OTHER PUBLICATIONS

Ishino et al. Amniotic Membrane as a Carrier for Cultivated Human Corneal Endothelial Cell Transplantation. Invest Ophthalmol Vis Sci. 2004;45:800-80.
English translation of JP 2001161353 A.translated on Aug. 29, 2011. p. 1-7.

* cited by examiner (a)

(b)

(c)

CELL-CONTAINING SHEET

CROSS-REFERENCE TO RELATED APPLICATIONS

This application is a Divisional of U.S. patent application Ser. No. 11/455,112, filed on Jun. 19, 2006, which claims priority from Japanese Patent Application No. 2005/178394 filed Jun. 17, 2005. The entire disclosures of the prior applications are considered part of the disclosure of the accompanying continuation application, and are hereby incorporated by reference

BACKGROUND OF THE INVENTION

1. Field of the Invention

The present invention relates to a cell-containing sheet that is useful as a medical implant, a method for producing the same, and a treatment method using the same.

2. Background Art

In recent years, a technology whereby artificial alternatives or organized culture cells are used for implantation has been under development and gaining attention. Representative examples of such alternatives or cells to be implanted include artificial skin, artificial blood vessels, and tissue composed of culture cells. In the case of artificial skin made of synthetic polymers, for example, rejection or the like might occur, therefore such skin is not preferable for implantation. Meanwhile, tissue composed of cultured cells is made by culturing and organizing cells of a patient. Thus, there is no concern about rejection when using such tissue in the patient himself/herself. Therefore, the tissue is preferable for implantation. Such tissue composed of cultured cells is produced by collecting cells from a patient and culturing the cells for the patient.

Many types of animal cells need to adhere to an object so as to proliferate, which is described as anchorage dependence. Thus, in vitro animal cells cannot live for a long period of time in a floating state. Therefore, in cell culture for producing the aforementioned tissue composed of cells, carriers, for example, a polymeric material such as modified polystyrene that has cell adhesiveness improved via surface treatment or culture dishes produced by uniformly applying a cell adhesion protein such as collagen or fibronectin to glass or a polymeric material have been used. Cells that have two-dimensionally adhered to such carriers are excellent in terms of capacity to be cultured; however, such cells are unlikely to be organized, in general. Thus, such cells lack their inherent functions. For instance, a study reported that the capacity of unorganized hepatocytes (cultured hepatocytes) to produce albumin is several times less than that of organized hepatocytes (liver spheroids).

Meanwhile, a technology has been reported whereby cultured cells are allowed to adhere to and are arranged only on minute areas on a substrate, resulting in enhanced cellular organization. In a method for arranging cultured cells, a substrate having surface patterns with different levels of ease of adhesion to cells is used, cells are cultured on the surface patterns, and the cultured cells are allowed to adhere exclusively to the surface patterns that have been processed in a manner such that cells can adhere thereto.

For instance, in JP Patent Publication (Kokai) No. 3-7576 A (1991), arrangement of cultured cells was attempted on a surface on which photosensitive hydrophilic polymers lacking or having cell adhesiveness were subjected to patterning via a photolithography method. Further, JP Patent Publication (Kokai) No. 5-176753 A (1993) discloses a substrate for cell culture on which patterns have been made using a substance such as collagen that influences cell adhesion ratio or cell form and a method for producing such substrate via photolithography. When cells are cultured on such substrate, many cells are allowed to adhere to the surface patterns formed with collagen and the like, resulting in implementation of cell patterning thereof.

When patterning is carried out by, for example, the aforementioned photolithography using a photosensitive material, extremely fine patterns can be obtained; however, cell adhesive materials are required to have photosensitivity. In such case, it is often difficult to carry out chemical modification so as to impart photosensitivity to biopolymers and the like. Thus the range of choices for cell adhesive materials is extremely narrowed, which has been problematic. In the case of photolithography using photoresists, a developing solution or the like must be used, and thus this has sometimes caused adverse effects upon cell culture. In addition, in general, biomaterials and other materials having high cell culture capacities are unlikely to be degraded via plasma, resulting in low industrial productivity upon patterning using a plasma etching method. Thus, such patterning is impractical.

Moreover, cells cultured via patterning as described above are subjected to treatment using proteinase such as trypsin or chemical agents so as to be collected. Thus, the treatment steps become complicated, resulting in a high probability of contamination. In addition, functions inherent to cells might be impaired as a result of cell degeneration or cell damage.

JP Patent Publication (Kokai) No. 2003-38170 discloses a method for producing a cell sheet, comprising the steps of: producing a cell culture support in which patterns have been formed on a substrate using temperature-responsive polymers; culturing cells on the cell culture support; allowing the cells to come into close contact with the polymer membrane; changing the temperature; and removing cells together with the polymer membrane from the support without causing damage to the cells. However, in accordance with the method disclosed in the above reference, adherence between the polymer membrane and cells is weak when cells are removed from the support together with the polymer membrane, so that it is difficult to form a cell sheet having fine patterns.

WO2005/038011 teaches a method for forming fine cell patterns on an implant site, comprising the steps of: allowing cells to adhere to the surface of a substrate for cell arrangement on which a cell adhesiveness-variation pattern containing cell adhesiveness promoted regions and cell adhesiveness inhibited regions has been developed; transferring the adhering cells in the patterned form to the implant site; and culturing the cells. However, in accordance with this method, after overlapping cells on the substrate for cell arrangement on the implant site, it is necessary to retain the substrate for cell arrangement while carrying out cell culture until cells become fixed on the implant site. Thus, it is difficult to apply such method to immediate implantation.

Meanwhile, a technique has been reported whereby cornea epithelial cells or conjunctival epithelial cells are cultured and organized on amnion from which the sponge layer and the epithelial layer have been removed such that cell fragments together with the amnion are used for implantation (JP Patent Publication (Kokai) No. 2001-161353 A). Since amnion has sufficient membrane strength and no antigenicity, it is convenient to use amnion as a support for cell fragments used for implantation. However, in accordance with the method disclosed in the above reference, it is impossible to arrange cells in fine patterns and to culture the cells.

SUMMARY OF THE INVENTION

It is an objective of the present invention to provide an implant in which cells are arranged in a fine pattern that is available for immediate implantation and that does not need to be removed after implantation.

As a result of intensive studies in order to solve the above problems, the inventors of the present invention have found that an implant having a fine cell pattern can be formed by: allowing cells to adhere to the surface of a substrate for cell arrangement in which a cell adhesiveness-variation pattern containing cell adhesiveness promoted regions and cell adhesiveness inhibited regions has been developed; and transferring the cells to a support comprising a bioabsorbable material. This has led to the completion of the present invention.

Specifically, the present invention encompasses the following inventions:

(1) a cell-containing sheet, which comprises cells and a support comprising a bioabsorbable material,
in which the support has a cell adhesion protein-containing layer on the surface thereof and the cells form a pattern on the cell adhesion protein-containing layer;

(2) the cell-containing sheet described in (1), in which the support is derived from amnion;

(3) the cell-containing sheet described in (1), in which the support comprises a biodegradable polymer material and the cell adhesion protein-containing layer adhering to the surface of the material;

(4) the cell-containing sheet described in any one of (1) to (3), in which the cells form cell junctions between each other;

(5) the cell-containing sheet described in any one of (1) to (4), in which the pattern formed with the cells has a width of not more than 3 mm;

(6) the cell-containing sheet described in (5), in which the pattern formed with the cells comprises lines having widths of 5 μm to 3 mm on which the cells are arranged;

(7) a method for producing a cell-containing sheet containing cells and a support comprising a bioabsorbable material that has a cell adhesion protein-containing layer on the surface thereof, comprising the steps of:
a) allowing cells to adhere to cell adhesiveness promoted regions on the surface of a substrate for cell arrangement, on which a cell adhesiveness-variation pattern containing cell adhesiveness promoted regions and cell adhesiveness inhibited regions has been developed;
b) allowing the substrate for cell arrangement to which cells have adhered in a pattern to come into contact with a cell adhesion protein-containing layer on the surface of the support such that the cells are allowed to adhere to the support; and
c) removing the substrate for cell arrangement from the support so as to transfer the cells to the support;

(8) the method described in (7), wherein the support is derived from amnion;

(9) the method described in (7), wherein the support comprises a biodegradable polymer material and the cell adhesion protein-containing layer adhering to the surface of the material;

(10) the method described in any one of (7) to (9), wherein the cell adhesiveness-variation pattern is formed with a cell adhesiveness-variable layer comprising a cell adhesiveness-variable material that experiences a change in cell adhesiveness due to photocatalytic action upon energy irradiation;

(11) the method described in (10), wherein the cell adhesiveness-variable layer is a photocatalyst-containing cell adhesiveness-variable layer comprising a photocatalyst and a cell adhesiveness-variable material;

(12) the method described in (10), wherein the cell adhesiveness-variable layer has a photocatalyst treatment layer containing photocatalyst and a cell adhesiveness-variable material layer containing a cell adhesiveness-variable material, which is formed on the photocatalyst treatment layer;

(13) the method described in (12), wherein the cell adhesiveness-variation pattern is formed by energy irradiation after placing the cell adhesiveness-variable layer that contains a cell adhesiveness-variable material and a photocatalyst-containing layer that contains a photocatalyst in a manner such that both layers are opposed to each other;

(14) a method for forming tissue in mammals by implanting the cell-containing sheet described in (1) into mammals;

(15) the method described in (14), comprising forming vascular tissue in mammals by implanting the cell-containing sheet comprising vascular endothelial cells into mammals;

(16) the method described in (14), comprising forming periodontal ligament into mammals by implanting the cell-containing sheet comprising periodontal ligament cells into mammals;

(17) a method for treating diseases in mammals by implanting the cell-containing sheet described in (1) into mammals;

(18) the method described in (17), comprising treatment of oral diseases of mammals by implanting the cell-containing sheet comprising periodontal ligament cells into mammals; and

(19) the method described in (17), comprising treatment of ischemic diseases of mammals by implanting the cell-containing sheet comprising vascular endothelial cells into mammals.

According to the present invention, an implant in which cells are arranged in a fine pattern, which is available for immediate implantation, and which does not need to be removed after implantation is provided.

This specification includes part or all of the contents as disclosed in the specification and/or drawings of Japanese Patent Application No. 2005-178394, which is a priority document of the present application.

BRIEF DESCRIPTION OF THE DRAWINGS

The patent or application file contains at least one drawing executed in color. Copies of the patent or patent application publication with color drawings will be provided by the office upon request and payment of the necessary fee.

EXPLANATION OF THE SYMBOLS

Figure 1:
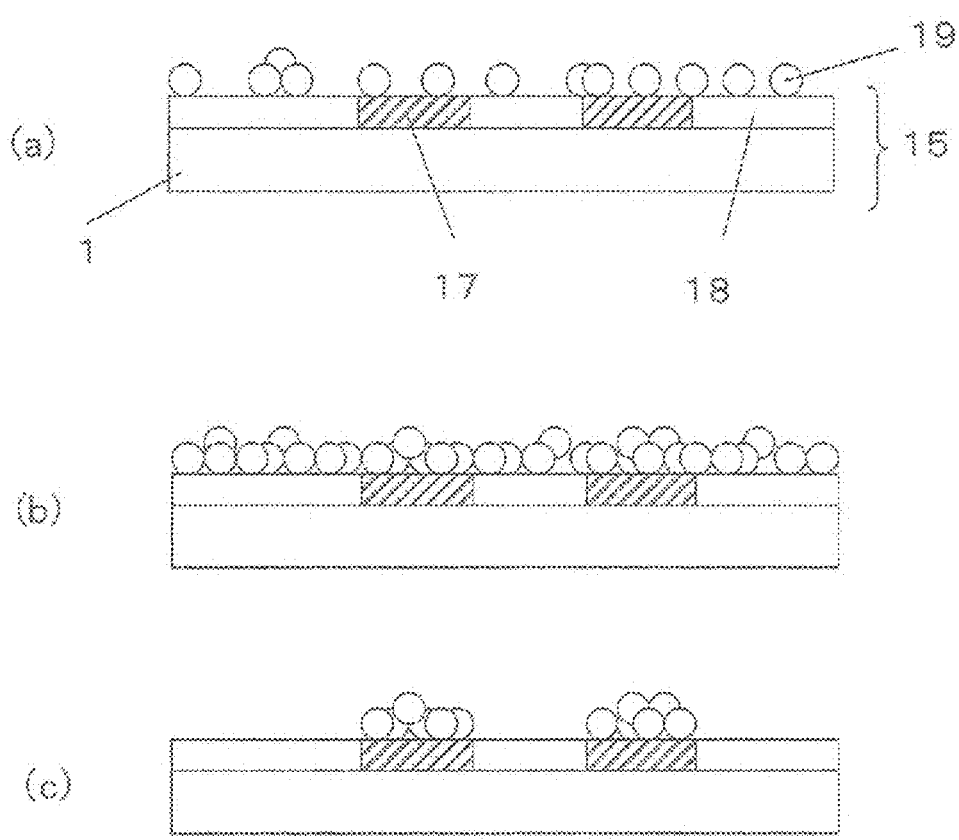
FIG. 1 shows the procedures of the present invention for allowing cells to adhere to a substrate for cell arrangement.

1: Substrate; 2: Photocatalyst-containing cell adhesiveness-variable layer; 3: Substrate for pattern formation; 4: Photomask; 5: Energy; 6: Cell adhesiveness-variable pattern; 7: Photocatalyst treatment layer; 8: Cell adhesiveness-variable material layer; 11: Support; 12: Photocatalyst-containing layer; 13: Photocatalyst-containing layer-side basal plate; 14: Photocatalyst-containing layer-side light shielding part; 15: Substrate for cell arrangement; 16: Cell adhesion protein-containing layer; 17: Cell adhesiveness promoted region; 18: Cell adhesiveness inhibited region; 19: Cells; 20: Water repellent material; 21: Cell adhesive material; 23: Support comprising a bioabsorbable material

DETAILED DESCRIPTION OF THE INVENTION

The present invention relates to a cell-containing sheet that comprises cells and a support comprising a bioabsorbable material. In the cell-containing sheet of the present invention, the support has a cell adhesion protein-containing layer on the surface thereof so that cells form a pattern, and preferably a fine pattern, on the cell adhesion protein-containing layer on the surface of the support.

The support comprising a bioabsorbable material is not particularly limited as long as: it has a cell adhesion protein-containing layer on the surface thereof; it is degraded and absorbed via in vivo hydrolysis, enzymatic degradation, or the like; and it has a certain level of mechanical strength. Such support that can be used is an organism-derived or synthetic support.

Such synthetic support comprising a bioabsorbable material that can be used contains a biodegradable polymer material and a cell adhesion protein-containing layer adhering to the surface of the material. The biodegradable polymer material is not particularly limited as long as it can be degraded and absorbed via in vivo hydrolysis, enzymatic degradation, or the like and as long as it has a certain level of mechanical strength. Preferred examples of such material that can be used include polyglycolic acid, polylactic acid, a copolymer of glycolic acid and lactic acid, polydioxanone, a copolymer of glycolic acid and trimethylene carbonate, and a mixture of polyglycolic acid and polylactic acid. The form of such biodegradable polymer material is not particularly limited and is designed in accordance with the purposes thereof. Examples thereof may include a sheet, a mesh sheet, a woven fabric, and a non-woven fabric. In order to place cells in a fine pattern, the biodegradable polymer material is preferably formed into a sheet. Preferably, the aforementioned biodegradable polymer is subjected to hydrophilic treatment by plasma irradiation or the like.

The support can be produced by allowing the cell adhesion protein-containing layer to adhere to the surface of the biodegradable polymer material. The cell adhesion protein-containing layer can be formed by applying a cell adhesion protein-containing solution to the surface of the biodegradable polymer material. For instance, a monolayer of cell adhesion proteins has a thickness of about 2 nm, a basal lamina in organism tissue has a thickness of about 50 to 100 nm, amnion has a thickness of about 0.1 mm, and a cornea has a thickness of about 0.5 mm. Considering these facts, the cell adhesion protein-containing layer is adjusted to have a thickness of about 2 nm to 2 mm and preferably of about 50 nm to 1 mm.

Cell adhesion proteins are proteins having a function of adhering to cells. Specific examples thereof include various types of collagens, fibronectins, laminins, vitronectins, cadherins, gelatins, fibrinogens, fibrins, and integrins. Preferably, the cell adhesion protein-containing layer of the present invention is a collagen-containing layer, since it is excellent in terms of cell adhesiveness.

Various types of conventionally used collagens can be used in the present invention. Examples thereof include neutral solubilized collagens, acid-soluble collagens, alkali-soluble collagens, and enzymatically solubilized collagens. Of these, alkali-soluble collagens and enzymatically solubilized collagens are preferably used. This is because they are obtained by allowing insoluble collagens to be subjected to alkaline treatment or enzymatic treatment using enzymes such as pepsin, trypsin, chymotrypsin, papain, and pronase, so that a telopeptide part in a collagen molecule that has strong antigenicity is removed, resulting in the reduced antigenicity.

Origins of these collagens are not particularly limited. In general, such collagens that can be used are obtained from skin, bones, cartilages, tendons, organs, or the like of mammals including primates such as humans and monkeys, rodents such as rabbits, mice and rats, pet animals such as canines and felines, bovines, swines, sheep, horses, and the like. In addition, collagen-like proteins obtained from fishes, birds, or the like also can be used.

In accordance with the present invention, the expression "support comprising a bioabsorbable material" indicates a structure having the cell adhesion protein-containing layer. In the case of an organism-derived support, the cell adhesion protein-containing layer may be an extracellular substrate layer that originally exists on tissue within organism.

The organism-derived support is not particularly limited as long as it is derived from membranous tissue in vivo and it has a low level of antigenicity. Examples thereof include an amnion-derived support and a chorion-derived support. Preferably, such support that serves as an implant does not induce immunoreactions. Thus, a membrane that contains no cells or a membrane from which cells have been removed is preferably used. This is because cells may have antigenicity so as to induce immunoreactions. The most preferred example of the organism-derived support of the present invention is an amnion-derived support. Amnion does not contain vascular components, so it is unlikely to induce rejection. Thus, amnion is preferable as an implant material.

Amnion or chorion may be collected in the manner described in JP Patent Publication (Kokai) No. 5-56987 A (1993), for example. Specifically, the fetal membrane is exclusively separated from the fetal membrane combined with placenta and umbilical cord immediately after delivery using a 1% benzalkonium chloride solution or benzalkonium bromide solution. Then, the amnion or chorion is removed from the fetal membrane comprising four layers. Thereafter, residual tissue and the like are physically or enzymatically removed therefrom, followed by ultrasonic cleaning. Thus, the purified amnion or chorion can be obtained.

Amnion in vivo is composed of an epithelial layer, basal lamina, stratum compactum, a fibroblast layer, and stratum spongiosum. Preferably, a layer composed of cells is removed from the amnion in vivo such that a membrane comprising stratum compactum and basal lamina is used as an amnion-derived support. Since basal lamina is rich in collagen, it functions as a cell adhesion protein-containing layer in an organism-derived support comprising stratum compactum and basal lamina. Also, since stratum compactum is rich in collagen, it can function as a cell adhesion protein-containing layer and a membrane consisting of stratum compactum may be used as the support of the present invention. The cell layer may be removed from amnion in the manner described in JP Patent Publication (Kokai) No. 2001-161353 A, for example. Specifically, amnion collected as described above is pretreated with 10% ammonia water such that a cell layer such as an epithelial layer can be readily removed.

The membrane comprising stratum compactum and basal lamina serving as the amnion-derived support may be supported by the aforementioned biodegradable polymer material. Specifically, in accordance with the present invention, examples of the support comprising a biodegradable material include a support in which an organism-derived membrane such as amnion is allowed to adhere to the biodegradable polymer material. In such case, such organism-derived membrane can be adhered to the biodegradable polymer material using cell adhesion proteins such as collagens serving as an adhesive.

In addition, when the support has cell adhesiveness, the support functions as a support containing a cell adhesion protein-containing layer. Examples thereof include a collagen membrane and a laminin membrane.

In the cell-containing sheet of the present invention, cells form a pattern on the cell adhesion protein-containing layer on the surface of the aforementioned support comprising a bioabsorbable material. Preferably, the cell adhesion protein-containing layer is not subjected to any patterning treatment such as resist printing and plasma surface treatment. Thus, possible toxicity as well as cell adhesion inhibition due to resist and possible thermal denaturation induced on a cell adhesion protein-containing layer via plasma treatment can be avoided. Preferably, cells contained in the cell-containing sheet of the present invention have adhesiveness. Examples of such cells include hepatocytes, which are liver parenchymal cells; endothelial cells such as vascular endothelial cells and endothelial corneal cells; epidermal cells such as fibroblasts and keratinized epidermal cells; epithelial cells such as tracheal epithelial cells, gastrointestinal epithelial cells and cervical epithelial cells; mammary cells; myocytes such as smooth muscle cells and cardiomyocytes; renal cells; Langerhans cells of the pancreas; neurocytes such as peripheral neurocytes and optic nerve cells; chondrocytes; and osteocytes. In accordance with the present invention, particularly preferably, cells such as vascular endothelial cells, neurocytes, lymphangial cells, and periodontal ligament-derived cells are used since such cells are arranged in a pattern, resulting in promoted cellular organization. Such cells may be primary cells directly collected from tissue or organs. Alternatively, such cells may be obtained through subinoculations or differentiation by culture. That is, cells used in the present invention may be any cells selected from undifferentiated ES cells, pluripotent stem cells having pluripotency, unipotent stem cells having unipotency, and differentiated cells.

Specific examples of blood vessels from which vascular endothelial cells can be collected include great vessels to microvessels such as the carotid artery, the umbilical vein and vessels in omental. Examples of cells that are differentiated into vascular endothelial cells via culture include: vascular endothelial cell precursor cells contained in bone marrow, umbilical cord blood, and peripheral blood; fat cells; and ES cells. Such cells may form a cell pattern comprising different types of cells.

Periodontal ligament cells are generally cells contained in periodontal ligament. Examples thereof include fibroblasts, vascular endothelial cells, osteoblasts, osteoclasts, and cementoblasts. Such cells can be collected from periodontal ligament (The Anatomical Record vol. 262, 193-202, 2001).

The pattern formed on the cell-containing sheet of the present invention is not particularly limited as long as it is a two-dimensional pattern. Examples of such pattern that can be formed include a line-form pattern; a tree-form (dendritic form) pattern; a mesh pattern; a lattice pattern; a round pattern; a square pattern; a pattern containing round, square, and different-shaped forms, the insides of which contain cells scattered thereon; and a pattern in which a plurality of round, polygonal, and different-shaped regions are arranged. The present invention is advantageous in terms of its capacity to form an especially fine pattern. In accordance with the present invention, it is possible to form a fine pattern on a support. It has been impossible to form such pattern by conventionally carried out dropping or dispersion of a cell suspension. Specifically, the cell-containing sheet of the present invention is distinguished from conventional cell sheets since it contains a fine pattern at least on a part thereof. Such fine pattern is, for example, a pattern not more than 3 mm in size, preferably a line-form pattern 5 µm to 3 mm in width, and more preferably a line-form pattern 5 to 500 µm in width, upon which cells are arranged. Examples of lines in such fine pattern include curved lines and straight lines in a tree-form pattern, a mesh pattern, and a lattice pattern. The fine pattern that may be used is a pattern in which cells are arranged in a plurality of regions not more than 3 mm in size and in which the regions are uniformly arranged. Such regions not more than 3 mm in size include polygonal (e.g., square or triangle) regions having sides of preferably 5 µm to 2 mm and more preferably 5 to 500 µm and round regions having diameters of preferably 5 µm to 3 mm and more preferably 5 to 500 µm.

In a pattern that is formed by the present invention, unlike the case where cells are merely dispersed, cells are arranged in a pattern so as to interact with each other. Cells are organized by interacting with each other, resulting in improved cell viability. Thus, the cell-containing sheet can efficiently be produced.

In the case of vascular endothelial cells, neurocytes, lymphangial cells, or the like, cells are arranged in a line form, a tree form (dendritic form), a mesh form, or a lattice form such that cellular organization is enhanced, resulting in promotion of vascular or neuron formation. Specifically, the line width required for cell arrangement is generally 5 to 500 µm and preferably 20 to 300 µm. The line width required for a cell-free space is generally 20 to 500 µm and preferably 40 to 300 µm. Alternatively, such line may have a width that can accommodate about 1 to 50 cells and preferably about 2 to 30 cells. When the line width is defined so as to fall within the numerical range described above, vascular endothelial cells are allowed to efficiently achieve vascular organization. Upon formation of a cell adhesiveness-variation pattern, vascular endothelial cells that have adhered in a line form and have been transferred are organized such that capillaries are efficiently formed into a line. When a cell pattern in which a plurality of lines are formed in parallel without crossing over each other is required, the width of the space between lines to which cells have adhered is determined to exceed a certain level as described above such that it prevents lines from being distorted due to pseudopodium extending from cells into the space between lines during cells are organized.

In addition, when vascular endothelial cells are arranged in a lattice form so as to be cultured such that capillaries are formed, lines and spaces are alternatively arranged as described above, and lines in which cells are arranged intersect with such lines. In such case, the line widths of lines that intersect with each other are as described above. Herein, the width of a space between lines is generally 0.03 to 5 cm and preferably 0.04 to 3 cm.

Diameters of artificial blood vessels in past reports have not been less than 4 mm. Thus, it has been difficult to produce artificial capillaries having diameters of less than 4 mm. However, in accordance with the present invention, a cell-containing sheet in which cells are arranged in a fine pattern is provided. Thus, capillary formation and immediate implantation can be realized.

In the case of periodontal ligament cells or fibroblasts, a pattern in which cells are arranged in a plurality of very small regions and in which the regions are uniformly arranged is preferable. Examples of such pattern include a pattern in which a plurality of regions uniformly exist and the regions contain cells arranged therein. Specifically, such regions are polygonal (e.g., square or triangle) regions having sides of preferably 5 µm to 2 mm and more preferably 5 to 500 µm and round regions having diameters of preferably 5 µm to 3 mm and more preferably 5 to 500 µm.

When cells are arranged in such a manner, cellular organization is enhanced. For instance, when periodontal ligament cells are organized, periodontal ligament is formed. In addition, when fibroblasts are organized, connective tissue is formed.

The present invention also relates to a method for implanting the aforementioned cell-containing sheet into mammals. The support used for the cell-containing sheet of the present invention comprises a biodegradable material so that it is degraded and absorbed in vivo. Thus, unlike the conventional cases, there is no need to remove such support via a subsequent operation or endoscopy. Examples of mammals into which the cell-containing sheet of the present invention can be implanted include primates such as humans and monkeys, rodents such as rabbits, mice, and rats, pet animals such as canines and felines, bovines, swine, sheep, and horses.

Upon implantation of the cell-containing sheet of the present invention, either the support side or the cell side is allowed to come into contact with an implant site. When an implant site has a cell adhesion protein-containing layer such as a basal lamina, implantation is preferably carried out by allowing the support side of the cell-containing sheet of the present invention to come into contact with the implant site. This is because degradation and absorption of the support comprising a bioabsorbable material can be accelerated. When an implant site does not have a cell adhesion protein-containing layer, in view of promotion of adhesion of the cell-containing sheet to the implant site, implantation is preferably carried out by allowing the cell side or the cell adhesion protein-containing layer side of the cell-containing sheet of the present invention to come into contact with the implant site.

In the case of organ transplantation, capillaries are formed on the surface of a transplanted organ after transplantation. It has been known that transplantation can be effectively carried out by a technique whereby capillaries are preoperatively formed on the surface of the organ to be transplanted. However, via a method using such conventional technique wherein capillaries are preoperatively formed so as to be allowed to adhere to the surface of the organ to be transplanted, it is impossible to immediately carry out transplantation due to the time-consuming nature of capillary formation. Further, when blood vessels that have been preoperatively formed on a culture substrate are removed from the substrate so as to be transferred to the surface of the organ, the blood vessel tissue becomes damaged. Since the cell-containing sheet of the present invention can be implanted as it is, there is no need to remove blood vessels formed on a substrate, resulting in no damage to the tissue. In addition, even in a case where the cell-containing sheet of the present invention is implanted in a state wherein complete vascular tissue formation has not been achieved on the support, in vivo cellular organization is promoted, leading to vascular formation. This is because cells are arranged in a pattern on the cell-containing sheet. Thus, immediate implantation can be achieved.

Moreover, the present invention relates to a method of forming tissue and treating diseases, comprising implanting the cell-containing sheet of the present invention into mammals. Implantation of the cell-containing sheet into mammals encompasses implantation of an organ or tissues to which the cell-containing sheet has adhered into mammals. When the cell-containing sheet of the present invention is implanted into mammals, cells contained in the sheet form the corresponding tissue such that damaged tissue can be regenerated. In addition, it is possible to form necessary tissues around the transplanted organ. Therefore, the present invention also relates to a method for treating damaged tissues by implanting the cell-containing sheet of the present invention into mammals.

Vascular tissues can be formed in mammals by implanting the cell-containing sheet containing vascular endothelial cells into mammals. Diseases such as ischemic diseases in mammals can be treated by implanting the cell-containing sheet containing vascular endothelial cells into mammals, resulting in vascular tissue formation. Periodontal ligament can be formed in mammals by implanting the cell-containing sheet containing periodontal ligament-derived cells into mammals. Oral diseases such as periodontal diseases in mammals can be treated by implanting the cell-containing sheet containing periodontal ligament-derived cells into mammals, resulting in periodontal ligament formation. Corium tissue or epidermis tissue can be formed in mammals by implanting the cell-containing sheet containing fibroblasts and epidermal cells such as keratinized epidermal cells into mammals. Wounds such as burn injuries and bed sores can be treated through such corium tissue or epidermis tissue formation. Epithelial tissue can be formed in mammals by implanting the cell-containing sheet containing epithelial cells such as tracheal epithelial cells, gastrointestinal epithelial cells, and cervical epithelial cells into mammals. Diseases such as ulcers can be treated through such epithelial tissue formation. Muscle tissue can be formed in mammals by implanting the cell-containing sheet containing myocytes such as smooth muscle cells and cardiomyocytes into mammals. Muscle diseases such as myocardial infarction can be treated through such muscle tissue formation. Nerve tissue can be formed in mammals by implanting the cell-containing sheet containing neurocytes such as peripheral neurocytes and optic nerve cells into mammals. Neural diseases such as nerve deficiency can be treated through such nerve tissue formation. Bone tissue can be formed in mammals by implanting the cell-containing sheet containing chondrocytes and osteocytes into mammals. Disease related to bone injuries such as bone injuries and cartilage injuries can be treated through such bone tissue formation.

Also, the present invention relates to a method for producing the aforementioned cell-containing sheet. Specifically, the present invention relates to a method for producing a cell-containing sheet that comprises cells and a support comprising a bioabsorbable material, where such support has a cell adhesion protein-containing layer on the surface thereof, comprising the steps of:

a) allowing cells to adhere to cell adhesiveness promoted regions on the surface of a substrate for cell arrangement on which a cell adhesiveness-variation pattern containing cell adhesiveness promoted regions and cell adhesiveness inhibited regions has been developed;

b) allowing the substrate for cell arrangement to which cells have adhered in a pattern to come into contact with a cell adhesion protein-containing layer on the surface of the support such that the cells are allowed to adhere to the support; and c) removing the substrate for cell arrangement from the support so as to transfer the cells to the support.

During step a), the cells are seeded on the substrate for cell arrangement, on which a cell adhesiveness-variation pattern containing cell adhesiveness promoted regions and cell adhesiveness inhibited regions has been developed such that the cells are allowed to adhere to cell adhesiveness promoted regions on the surface thereof. Preferably, a culture sample containing cells of interest is previously subjected to separation treatment whereby organism tissue is pulverized so as to be dispersed in a solution or dispersion treatment whereby cells other than cells of interest and impurities such as cell fragments in organism tissue are removed, for example.

Before cells are seeded on the substrate for cell arrangement, it is preferable to allow a culture sample containing cells of interest to be subjected to preliminary culture using various culture methods such that the cells of interest will proliferate. For preliminary culture, conventional culture methods such as monolayer culture, culture using a coat dish, gel culture, microcarrier culture, and three-dimensional culture in porous carriers can be adopted. Upon preliminary culture, a method for culturing cells by allowing them to adhere to the surface of a vessel is a technique known as a so-called monolayer culture method. Specifically, in accordance with such method, for example, a culture sample and a culture solution are accommodated in a culture vessel and the vessel is maintained under stable environmental conditions, so that specific viable cells exclusively proliferate while adhering to the surface of the culture vessel. Regarding the apparatus used or treatment conditions, general monolayer culture methods and the like can be referred to. As a material of the surface of the vessel to which cells adhere so as to proliferate, a material comprising polylysine, polyethyleneimine, collagen, gelatin, or the like with which good cell adhesion or cell growth can be attained may be selected. Alternatively, so-called cell adhesion factors, which are chemical substances with which good cell adhesion or cell growth can be attained, may be applied to the surface of a support such as a glass petri dish, a plastic petri dish, a slide glass, a cover glass, a plastic sheet, or a plastic film.

The culture solution in the culture vessel is removed after culture so as to remove unwanted components such as impurities in the culture sample, which form a mass or fiber that does not adhere to the surface of the vessel, such that viable cells that adhere to the surface of the vessel can be exclusively collected. A means such as EDTA-trypsin treatment can be applied to collection of viable cells that adhere to the surface of the vessel.

Cells subjected to preliminary culture as described above were seeded on a substrate for cell arrangement (15) in a culture solution as shown in FIG. 1 ($a$). A method for seeding cells and the amount of cells seeded are not particularly limited. For instance, a method described in Tissue Culture Technology (Soshiki-baiyo no gijutsu), 1999, edited by the Japanese Tissue Culture Association, pp. 266 to 270 (Asakura Publishing Co., Ltd.) can be used. Preferably, cells are seeded on the substrate for cell arrangement in a sufficient amount such that the cells do not need to proliferate on the substrate, resulting in monolayer cell adhesion. In general, preferably, cells are seeded in an order such that the cells are contained in the culture solution at a density of $10^4$ to $10^6$ cells/ml. In addition, preferably, cells are seeded in an order such that the cells are contained in the substrate at a density of $10^4$ to $10^6$ cells/cm$^2$. This is because cell aggregation prevents cellular organization such that cell function deteriorates even after cells are transferred to the support, followed by culture. Specifically, cells are seeded on the support at a density of about $2 \times 10^5$ cells/400 mm$^2$.

Preferably, a substrate for cell arrangement on which cells have been seeded is cultured in a culture solution such that cells are allowed to adhere to cell adhesiveness promoted regions. As a culture solution, a medium that can be generally used in the art may be used. Examples of such culture solution that can be used include, depending on the type of cells to be used, minimal essential media such as an MEM medium (Eagle's Minimum Essential Medium), an EBM medium (Eagle's Basal Medium), a DMEM medium (Dulbecco's Modified Eagle's Medium), an aMEM medium (Stanners' Modified Eagle's Minimum Essential Medium), an IMDM medium (Iscove's Modified Dulbecco's Medium), a ES medium (Koyama's Modified Eagle's Minimum Essential Medium), DM-160 medium (Katsuta's Denken Medium 160), Fisher medium (Fisher's Medium for Leukemic Cells of Mice), an F12 medium (Ham's Medium F12), a WE medium (Williams' Medium E), and an RPMI medium (Roswell Park Memorial Institute's Medium 1640) described in Tissue Culture Technology (Soshiki-baiyo no gijutsu), third edition, edited by the Japanese Tissue Culture Association, p. 581 (Asakura Publishing Co., Ltd.). Further, these media supplemented with a serum component (e.g., fetal bovine serum) or the like and commercially available serum free media such as a Gibco serum free medium (Invitrogen) can be used.

As shown in FIG. 1 (b), an objective of the step of culturing cells is to allow cells to adhere to cell adhesiveness promoted regions of a substrate for cell arrangement. The time period for cell culture is not particularly limited, as long as it is long enough for cell adhesion. The period ranges generally from 16 to 30 hours and preferably from 20 to 24 hours. Cells are cultured for an adequate time period such that cells on cell adhesiveness inhibited regions of a substrate for cell arrangement are washed away upon washing, and at the same time, cells remain on cell adhesiveness promoted regions of a substrate for cell arrangement with adequate adhesiveness. Thus, it becomes possible to readily transfer remaining cells to a support comprising a bioabsorbable material that has a cell adhesion protein-containing layer.

Cell culture is carried out at a temperature of 37° C., in general. Preferably, cell culture is carried out under a $CO_2$ atmosphere using a $CO_2$ incubator or the like. After culture, a substrate for cell arrangement is washed such that non-adherent cells are washed away, resulting in cell arrangement in a pattern (FIG. 1 (c)).

When a cell adhesiveness-variation pattern in which regions are formed having cell adhesiveness optimal for each type of cell to be arranged in a pattern, is developed on a substrate for cell arrangement, it is possible to allow a plurality of types of cells to adhere in a desired pattern to a single substrate for cell arrangement.

A substrate for cell arrangement in which a cell adhesiveness-variation pattern containing cell adhesiveness promoted regions and cell adhesiveness inhibited regions has been developed will be described below.

During step b), the substrate for cell arrangement to which cells have adhered in a pattern and a cell adhesion protein-containing layer on the surface of a support are allowed to come into contact with each other such that cells are allowed to adhere to the support. An outline of procedures for cell transfer according to the present invention is shown in FIG. 2.

Figure 2:
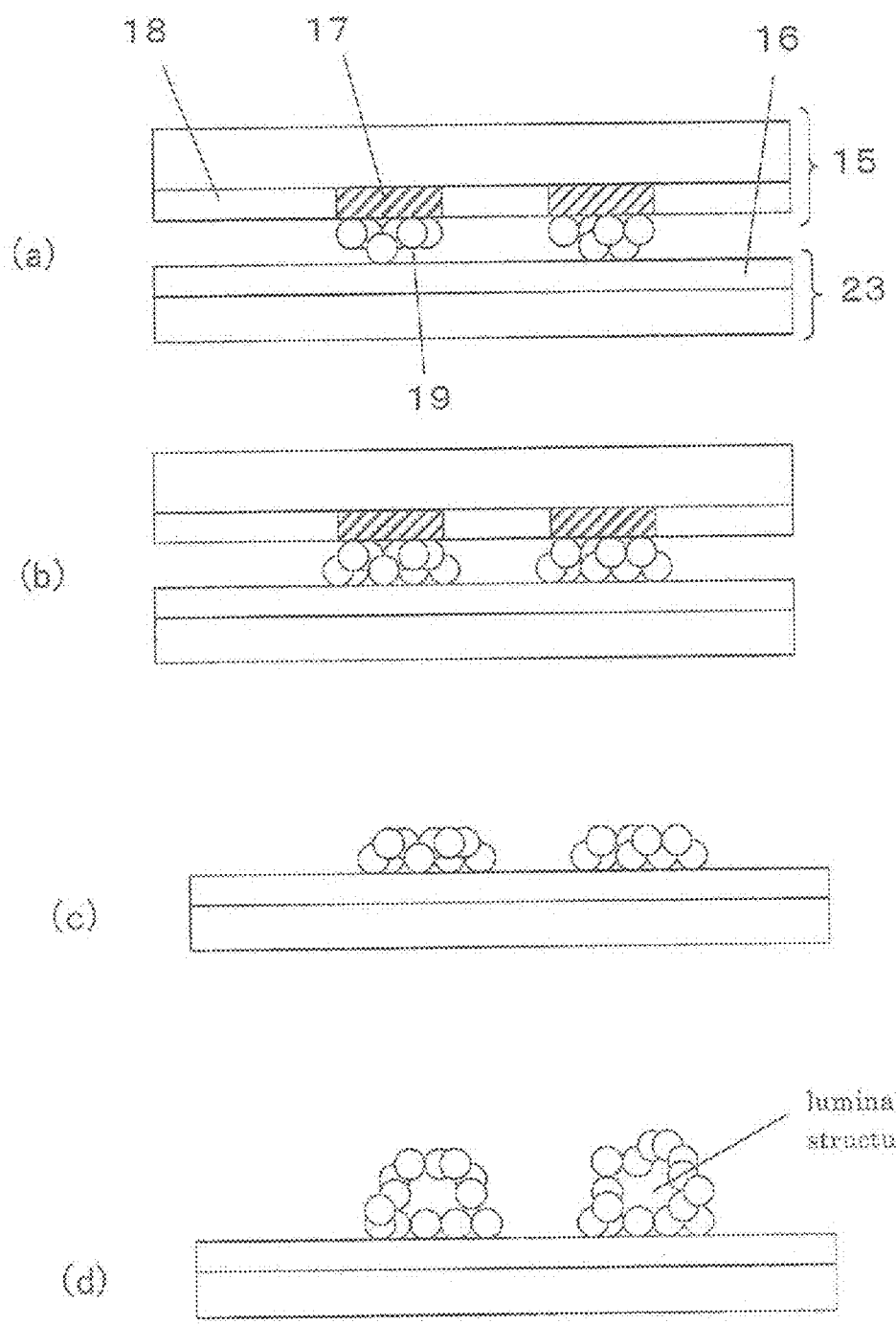
FIG. 2 shows the procedures of the present invention for transferring cells to a support for cell cultivation.

As shown in FIG. 2 (a), a substrate for cell arrangement in which cells adhere to cell adhesiveness promoted regions is allowed to come into close contact with a cell adhesion protein-containing layer on the surface of a support comprising a bioabsorbable material. Then, as shown in FIG. 2 (b), cells are cultured so as to adhere to the cell adhesion protein-containing layer of the surface of the support. Further, since cell adhesiveness of the cell adhesiveness promoted region is weaker than cell adhesiveness of the cell adhesion protein-containing layer, cells are transferred to the support when the substrate for cell arrangement is removed from the support as shown in FIG. 2 (c). Preferably, cell culture is carried out while the substrate for cell arrangement is allowed to come into close contact with the support. During cell culture, the polarities of cells vary such that cell adhesion to the support is promoted. In general, cell culture is carried out at 37° C. under a $CO_2$ concentration of 5% for 3 to 96 hours. After the substrate is removed, transferred cells are further cultured such that, as shown in FIG. 2 (d), cells are organized and functionalized. At such time, in the case of vascular endothelial cells, a circular structure is reproduced. Herein, a culture solution as described above can be used. In addition, while the substrate for cell arrangement is in close contact with the support for cell culture, interaction between cells and the substrate for cell arrangement becomes substantially lost such that cells may be functionalized or organized.

When transferred cells are cultured, cellular activity can be improved or functions inherent to cells can be expressed and cellular organization can be promoted by adding a cell stimulating factor. As such cell stimulating factor, any substance having activity of promoting cellular organization can be used. Examples thereof include a vascular endothelial cell growth factor (VEGF), a fibroblast growth factor (FGF), a nerve growth factor (NGF), an epithelial cell growth factor (EGF), and an insulin-like growth factor (IGF).

A substrate for cell arrangement in which a cell adhesiveness-variation pattern containing cell adhesiveness promoted regions and cell adhesiveness inhibited regions has been developed will be hereafter described in detail.

1. Substrate for Cell Arrangement

The substrate for cell arrangement of the present invention is characterized in that it has a cell adhesiveness-variation pattern formed thereon, which consists of cell adhesiveness promoted regions and cell adhesiveness inhibited regions.

The term "cell adhesiveness" indicates the cell adhesion strength, which in turn indicates the ease of cell adhesion. The term "cell adhesiveness promoted region" indicates a region which has good cell adhesiveness. The term "cell adhesiveness inhibited region" indicates a region which has poor cell adhesiveness. Thus, when cells are seeded on the substrate for cell arrangement having the cell adhesiveness-variation pattern, cells adhere to cell adhesiveness promoted regions, while on the other hand, they do not adhere to cell adhesiveness inhibited regions. As a result, cells are arranged in a pattern on the surface of the substrate for cell arrangement.

Since cell adhesiveness may vary depending on the type of cells that are caused to adhere, good cell adhesiveness means a condition where good cell adhesiveness is obtained with the use of cells of a certain type. Thus, a plurality of cell adhesiveness promoted regions corresponding to a plurality of cell types may exist on the substrate for cell arrangement, that is cell adhesiveness promoted regions having two or more different levels of cell adhesiveness may exist.

The cell adhesiveness-variation pattern is obtained in a manner such that a cell adhesiveness-variable layer containing a cell adhesiveness-variable material that experiences a change in cell adhesiveness upon energy irradiation is formed on a substrate, cell adhesiveness is allowed to vary upon energy irradiation on a certain region thereof, and regions having different levels of cell adhesiveness are formed into a pattern. Examples of such cell adhesiveness-variable material include a material that obtains cell adhesiveness or has an increased level of cell adhesiveness and a material that loses cell adhesiveness or has a decreased level of cell adhesiveness as a result of energy irradiation.

A substrate used as the substrate for cell arrangement of the present invention is not particularly limited as long as it is made of a material with which the cell adhesiveness-variation pattern can be formed on the surface thereof. Specific examples of such material include: inorganic materials such as metals, glasses, and silicones; and organic materials represented by plastics. The form thereof is also not limited. Examples of such form include flat plates, flat membranes, films, and porous membranes.

The average pore size of such porous membrane depends on cell type. In general, it is preferably 0.1 to 5 µm and more preferably 0.2 to 1.5 µm. When the pore size is not less than 0.1 µm, nutrition and humoral factors can be efficiently supplied to cultured cells. In addition, when the pore size is not more than 5 µm, it is possible to prevent cultured cells from adhering to the insides of pores or the backside of the membrane such that cultured cells can be efficiently transferred to the support.

The cell adhesiveness-variable material and the cell adhesiveness-variable layer will be described in the embodiment below in which a photocatalyst is used.

In addition, the cell adhesiveness-variation pattern may be formed in a manner such that the cell adhesive layer that contains a cell adhesive material having cell adhesiveness is formed on a cell adhesion inhibited layer that contains a cell adhesion-inhibiting material having decreased cell adhesiveness, then the cell adhesive layer is degraded and disappears due to energy irradiation and the cell adhesion inhibited layer is exposed, resulting in formation of regions that differ in terms of cell adhesiveness. Likewise, the cell adhesiveness-variation pattern may be formed in a manner such that the cell adhesion inhibited layer is formed on the cell adhesive layer, such that the cell adhesion inhibited layer is degraded and disappears due to energy irradiation, and the cell adhesive layer is exposed, resulting in formation of regions that differ in terms of cell adhesiveness.

Examples of such cell adhesive material include: various types of extracellular matrice such as collagen, fibronectin, laminin, vitronectin, and cadherin; RGD peptides; and polyolefin resins into which a carbonyl group or carboxyl group is introduced such that cell adhesiveness is imparted using techniques such as plasma treatment, corona treatment, ion beam irradiation treatment, and electron beam irradiation treatment. Examples of such cell adhesion-inhibiting material include fluorine materials such as polytetrafluoroethylene (PTFE); polyimide; and phospholipid.

Further, with the use of a method such as an inkjet method, the cell adhesiveness-variation pattern may be formed in a manner such that a cell adhesive material is allowed to adhere to a cell adhesion inhibited layer in a patterned manner or a cell adhesion-inhibiting material is allowed to adhere to a cell adhesive layer in a patterned manner.

Figure 3:
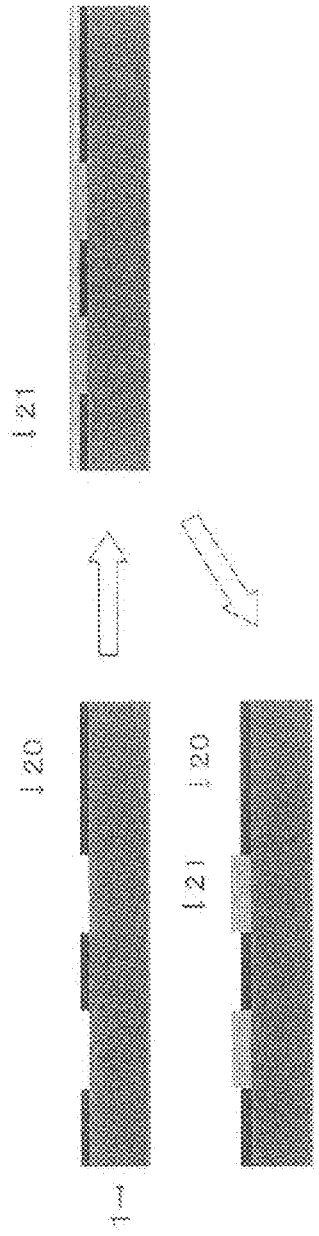
FIG. 3 shows the procedures of the present invention for allowing cells to adhere to a substrate for cell arrangement.
Figure 3:
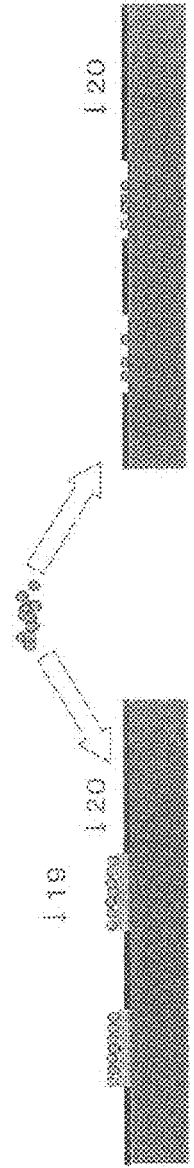

Alternatively, it is possible to form a cell adhesiveness-variation pattern that contains regions in which a cell adhesive material exists (cell adhesiveness promoted regions) and regions in which a cell adhesive material does not exist (cell adhesiveness inhibited regions) in a manner such that: a layer that contains an affinity-variable material that experiences a change in affinity to a cell adhesive material upon energy irradiation is additionally formed on a substrate; a pattern that contains regions having affinity to a cell adhesive material and regions having no affinity to a cell adhesive material is formed via energy irradiation; and a liquid containing a cell adhesive material is introduced into the pattern, followed by washing. In such embodiment, a pattern can be formed using a cell adhesive material that cannot be directly formed into a pattern on a substrate. For instance, as shown in FIG. 3a, a pattern that contains regions that comprise a layer containing water repellent material (20) and regions that does not comprise such layer is formed on a hydrophilic substrate (1) that is made of glass or the like. Then, a hydrophilic cell adhesive material (21) that is unlikely to adsorb to a water-repellent material is introduced into the pattern, followed by washing. Accordingly, a pattern containing regions in which a hydrophilic cell adhesive material exists (cell adhesiveness promoted regions) and regions in which a water-repellent material exists (cell adhesiveness inhibited regions) is formed. In such case, examples of the hydrophilic cell adhesive material that can be used include an extracellular substrate such as collagen or the like. When cells are seeded on such substrate so as to be subjected to washing, cells selectively adhere to cell adhesiveness promoted regions (FIG. 3b, left). If a water-repellent material is just removed, cell adhesion does not occur. Even if cell adhesion could occur, it would result in poor cell adhesion efficiency and poor cell transfer efficiency (FIG. 3b, right).

In accordance with the present invention, cells that are arranged in a pattern on a substrate for cell arrangement are transferred to a support having a cell adhesion protein-containing layer. Thus, preferably, the aforementioned cell adhesiveness promoted regions have appropriate cell adhesion strength. With such appropriate adhesion strength, cells are allowed to selectively adhere to certain regions such that a cell pattern is formed. Then, such pattern can readily be transferred to a cell adhesion protein-containing layer. Therefore, it is preferable that the cell adhesion strength of a cell adhesiveness promoted region on a substrate for cell arrangement be stronger than that of a cell adhesiveness inhibited region and weaker than that of a cell adhesion protein-containing layer.

Such cell adhesion strength can be evaluated based on surface water contact angle. Preferably, the water contact angle on a cell adhesiveness promoted region in the cell adhesiveness-variation pattern of the present invention is 10° to 40°. With a water contact angle within such range, when cells are allowed to adhere to a substrate for cell arrangement so as to be transferred to a cell adhesion protein-containing layer, cells can adhere to the substrate for cell arrangement while forming a monolayer thereon and cells can be readily transferred to the cell adhesion protein-containing layer due to their weak adhesion to the substrate for cell arrangement. The term "contact angle" indicates an angle between a liquid surface and a solid surface (the angle formed by a droplet between a liquid-gas interface and a solid-liquid interface) at a position where the free surface of the quiescent liquid comes into contact with the wall of the solid.

The aforementioned water contact angle indicates measurement value obtained by a method for measuring a static contact angle, wherein a minute droplet is deposited dropwise on the surface of a material at ordinary atmospheric pressure using an instrument such as a syringe such that the angle between a liquid-gas interface on the surface of the droplet and a solid-liquid interface is observed using a magnifying glass or the like.

A means for forming a cell adhesiveness-variation pattern in which cell adhesiveness promoted regions and cell adhesiveness inhibited regions as described above are arranged in a pattern is not particularly limited. Examples of such means include: various types of printing methods such as a gravure printing method, a screen printing method, an offset printing method, a flexography method, and a contact printing method; methods using various types of lithography methods; inkjet methods; and techniques of three-dimensional shaping whereby fine grooves or the like are engraved. In the present invention, lithography methods using a photocatalyst, that is to say, a method wherein a photocatalyst and a cell adhesiveness-variable material that experiences a change in cell adhesiveness due to photocatalytic action upon energy irradiation are used, is preferably used such that a cell adhesiveness-variation pattern is formed via energy irradiation based on a required pattern. In such embodiment, without using a coating liquid that adversely affects cells, an extremely fine pattern can be formed via convenient steps. In addition, since there is no need to modify a cell adhesiveness-variable material, it is possible to broaden the options of such material. Thus, it is not problematic to use a biological cell adhesiveness-variable material that exhibits specific adhesiveness as described below.

The pattern to be formed is not particularly limited as long as it is a two-dimensional pattern. Such pattern is designed in accordance with a pattern on a cell-containing sheet to be produced. When a line-form pattern or a mesh pattern is formed, the width thereof is generally 5 to 500 µm and preferably 20 to 300 µm. In particular, when capillaries are formed in a manner such that vascular endothelial cells are arranged in a line form so as to be cultured, it is preferable to form a cell adhesiveness-variation pattern in which cell adhesiveness promoted regions serving as lines and cell adhesiveness inhibited regions serving as spaces are alternatively arranged such that vascular endothelial cells are allowed to adhere to the line-form pattern. In such embodiment, it is preferable to form a pattern that enables cell adhesion in a manner such that a single line has a 1- to 50-cell width and preferably 2- to 30-cell width. Specifically, the line width of a cell adhesiveness promoted region is generally 5 to 500 µm and preferably 20 to 300 µm, and the width of the space that is a cell adhesiveness inhibited region between lines is generally 20 to 500 µm and preferably 40 to 300 µm. When the line width is within the numerical range described above, vascular organization of vascular endothelial cells is efficiently achieved.

For instance, when the line width of a cell adhesiveness promoted region is as wide as 100 to 500 µm, an auxiliary pattern may be formed in the cell adhesiveness promoted region. Such auxiliary pattern is a fine pattern that is formed in a cell adhesiveness promoted region. The auxiliary pattern may be a fine cell adhesiveness inhibited region. In addition, the auxiliary pattern is formed so as to have a certain area such that a fine cell adhesiveness inhibited region corresponding to the auxiliary pattern does not inhibit intercellular junctions in the cell adhesiveness promoted region when cells are allowed to adhere to the cell adhesiveness promoted region. That is to say, cells are also able to become bound to each other on the cell adhesiveness inhibited region corresponding to the aforementioned auxiliary pattern.

For instance, when vascular endothelial cells are allowed to adhere to a cell adhesiveness promoted region corresponding to a blood vessel pattern, cells are arranged in a stepwise manner from the vicinity of the border between a cell adhesiveness promoted region and a cell adhesiveness inhibited region to the inside of the cell adhesiveness promoted region. In general, upon tissue formation, it is necessary for each cell to experience morphological change so as to achieve cellular organization. Thus, also in the case of blood vessels, vascular endothelial cells experience morphological change in a manner such that the cells seem to be aligned toward the direction of a bloodstream. It is preferable that such morphological change be realized in vitro. However, as the line width of a cell adhesiveness promoted region becomes enlarged, the cell arrangement near the center of a cell adhesiveness promoted region tends to deteriorate compared with the cell arrangement near the border between a cell adhesiveness promoted region and a cell adhesiveness inhibited region. In addition, the density of adherent cells near the center of a cell adhesiveness promoted region tends to decrease. In order to improve such undesirable tendencies, the aforementioned auxiliary pattern is formed. With the use of the auxiliary pattern, cells that have adhered to any site in a cell adhesiveness promoted region are able to come into contact with the border between a cell adhesiveness inhibited region and a cell adhesiveness promoted region. Thus, the ratio of arranged adherent cells becomes very high. In addition, the auxiliary pattern described above is a fine pattern to such that adherent cells become bound to each other thereon. Thus, cells are allowed to uniformly adhere to the entirety of the cell adhesiveness promoted region at a high degree of orientation.

The auxiliary pattern described above is not particularly limited as long as it has an effect of allowing cells to become oriented in a desired direction. Examples of such pattern include a line-form pattern, a zigzag pattern, a convexoconcave pattern, and a dotted pattern. However, a line-form pattern is preferable. The line form is not particularly limited. Examples of such form that can be used include a straight line form, a curved line form, a dotted line form, and a dashed line form. The line width of the auxiliary pattern is 0.5 to 10 µm and preferably 1 to 5 µm. When the line width is within the above range, neighboring cells are able to become bound to each other in the auxiliary pattern so that cells are allowed to adhere to the entirety of the cell adhesiveness promoted region.

When such cell adhesiveness-variation pattern is formed, adhesion and transfer of vascular endothelial cells in a line form result in organization of the cells, leading to efficient formation of capillaries in a line form. When a cell pattern in which a plurality of lines are formed in parallel without crossing over each other is required, the width of the space between lines to which cell have adhered is determined to become larger than a certain level as described above. Accordingly, it becomes possible to prevent lines from being distorted due to pseudopodium extended from cells into the spaces between lines upon cellular organization.

Examples of a substrate for cell arrangement produced via lithography methods using the aforementioned photocatalyst are described in the following three embodiments. Hereafter, each embodiment will be described.

A. First Embodiment

In the first embodiment, the substrate for cell arrangement of the present invention has a cell adhesiveness-variable layer, which is formed on a substrate, and contains a cell adhesiveness-variable material that experiences a change in cell adhesiveness due to photocatalytic action upon energy irradiation. In addition, a cell adhesiveness-variation pattern in which cell adhesiveness is varied is formed on the cell adhesiveness-variable layer. The substrate for cell arrangement is characterized in that the cell adhesiveness-variable layer is a photocatalyst-containing cell adhesiveness-variable layer that contains a photocatalyst and the cell adhesiveness-variable material.

In this embodiment, as described above, the cell adhesiveness-variable layer is a photocatalyst-containing cell adhesiveness-variable layer that contains a photocatalyst and the aforementioned cell adhesiveness-variable material.

Thus, upon energy irradiation, the cell adhesiveness-variable material experiences a change in cell adhesiveness due to the action of a photocatalyst in the photocatalyst-containing cell adhesiveness-variable layer. Therefore, a cell adhesiveness-variation pattern in which areas subjected to energy irradiation and areas subjected to no energy irradiation differ in terms of cell adhesiveness can be formed.

Each member of the substrate for cell arrangement of this embodiment will be independently described.

1. Photocatalyst-Containing Cell Adhesiveness-Variable Layer

This embodiment is characterized in that a photocatalyst-containing cell adhesiveness-variable layer is formed on a substrate. Such photocatalyst-containing cell adhesiveness-variable layer at least has a photocatalyst and a cell adhesiveness-variable material.

(1) Cell Adhesiveness-Variable Material

The cell adhesiveness-variable material used in this embodiment is not particularly limited as long as it is a material that experiences a change in cell adhesiveness due to photocatalytic action upon energy irradiation. The expression "change in cell adhesiveness" corresponds to a case where a material obtains cell adhesiveness or has an increased level of cell adhesiveness due to photocatalytic action upon energy irradiation and a case where a material loses cell adhesiveness or has a decreased level of cell adhesiveness due to photocatalytic action upon energy irradiation.

In accordance with an embodiment in which cell adhesiveness is controlled, representative examples of such cell adhesiveness-variable material are a physicochemical cell adhesiveness-variable material that allows cells to adhere thereto based on its physicochemical properties and a biological cell adhesiveness-variable material that allows cells to adhere thereto based on its biological properties.

a. Physicochemical Cell Adhesiveness-Variable Material

Examples of physicochemical factors of a physicochemical cell adhesiveness-variable material that cause cells to adhere thereto include factors related to surface free energy and hydrophobic interaction.

Preferably, a physicochemical cell adhesive material that has physicochemical cell adhesiveness based on such factors has the main structure having a high level of binding energy such that it is not degraded by photocatalytic action, and it has organic substituents that are degraded by photocatalytic action. Examples of such material include organopolysiloxane (1), which exerts high strength and is obtained via hydrolysis and polycondensation of chlorosilane, alkoxysilane, or the like due to sol-gel reaction or the like, and organopolysiloxane (2) obtained via crosslinking of reactive silicone.

In the case of (1) above, organopolysiloxane is preferably a hydrolytic condensate or cohydrolytic condensate comprising at least one member of the group of silicon compounds represented by the following general formula:

(where Y represents alkyl, fluoroalkyl, vinyl, amino, phenyl, or epoxy, X represents alkoxyl, acetyl, or halogen, and n is an integer from 0 to 3). In addition, it is preferable that the carbon number of the group represented by Y range between 1 and 20 and that alkoxyl represented by X be methoxy, ethoxy, propoxy, or butoxy.

Moreover, as an organic group, polysiloxane containing fluoroalkyl is particularly preferably used. Specific examples thereof include a hydrolytic condensate and a cohydrolytic condensate of at least one fluoroalkylsilane described below:

$CF_3(CF_2)_3CH_2CH_2Si(OCH_3)_3$;
$CF_3(CF_2)_5CH_2CH_2Si(OCH_3)_3$;
$CF_3(CF_2)_7CH_2CH_2Si(OCH_3)_3$;
$CF_3(CF_2)_9CH_2CH_2Si(OCH_3)_3$;
$(CF_3)_2CF(CF_2)_4CH_2CH_2Si(OCH_3)_3$;
$(CF_3)_2CF(CF_2)_6CH_2CH_2Si(OCH_3)_3$;
$(CF_3)_2CF(CF_2)_8CH_2CH_2Si(OCH_3)_3$;
$CF_3(C_6H_4)C_2H_4Si(OCH_3)_3$;
$CF_3(CF_2)_3(C_6H_4)C_2H_4Si(OCH_3)_3$;
$CF_3(CF_2)_5(C_6H_4)C_2H_4Si(OCH_3)_3$;
$CF_3(CF_2)_7(C_6H_4)C_2H_4Si(OCH_3)_3$;
$CF_3(CF_2)_3CH_2CH_2SiCH_3(OCH_3)_2$;
$CF_3(CF_2)_5CH_2CH_2SiCH_3(OCH_3)_2$;
$CF_3(CF_2)_7CH_2CH_2SiCH_3(OCH_3)_2$;
$CF_3(CF_2)_9CH_2CH_2SiCH_3(OCH_3)_2$;
$(CF_3)_2CF(CF_2)_4CH_2CH_2SiCH_3(OCH_3)_2$;
$(CF_3)_2CF(CF_2)_6CH_2CH_2SiCH_3(OCH_3)_2$;
$(CF_3)_2CF(CF_2)_8CH_2CH_2SiCH_3(OCH_3)_2$;
$CF_3(C_6H_4)C_2H_4SiCH_3(OCH_3)_2$;
$CF_3(CF_2)_3(C_6H_4)C_2H_4SiCH_3(OCH_3)_2$;
$CF_3(CF_2)_5(C_6H_4)C_2H_4SiCH_3(OCH_3)_2$;
$CF_3(CF_2)_7(C_6H_4)C_2H_4SiCH_3(OCH_3)_2$;
$CF_3(CF_2)_3CH_2CH_2Si(OCH_2CH_3)_3$;
$CF_3(CF_2)_5CH_2CH_2Si(OCH_2CH_3)_3$;
$CF_3(CF_2)_7CH_2CH_2Si(OCH_2CH_3)_3$;
$CF_3(CF_2)_9CH_2CH_2Si(OCH_2CH_3)_3$; and
$CF_3(CF_2)_7SO_2N(C_2H_5)C_2H_4CH_2Si(OCH_3)_3$.

In general, polysiloxane known as a fluorinated silane coupler can be used.

When one of the forms of polysiloxane containing fluoroalkyl described above is used as a physicochemical cell adhesive material, areas not subjected to energy irradiation in a photocatalyst-containing cell adhesiveness-variable layer obtain a surface exhibiting no cell adhesiveness because of the existence of fluorine on the surface, and areas subjected to energy irradiation obtain a surface exhibiting cell adhesiveness because of the existence of hydroxy or the like as a result of removal of fluorine or the like. Thus, regions that differ in terms of cell adhesiveness, which are areas subjected to energy irradiation and areas not subjected to energy irradiation, can be formed in a patterned manner.

Examples of reactive silicone (2) above include compounds having the structure represented by the following general formula.

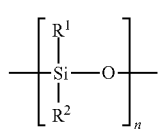

In the above formula, n is an integer of not less than 2, $R^1$ and $R^2$ independently represent a substituted or nonsubstituted $C_1$-$C_{10}$ alkyl, alkenyl, or aryl, and a substituent is halogen, cyano, or the like. Specific examples of $R^1$ and $R^2$ include methyl, ethyl, propyl, vinyl, phenyl, phenyl halide, cyanomethyl, cyanoethyl, and cyanopropyl. Of these, vinyl, phenyl, or phenyl halide preferably accounts for not more than 40% by mole of the compound. In addition, $R^1$ and $R^2$ are preferably methyl because this allows the lowest level of surface energy to be achieved. Thus, methyl preferably accounts for not less than 60% by mole. Further, the molecular chain has at least one reactive group such as hydroxyl on the chain end or in the side chain.

Furthermore, in addition to the aforementioned organopolysiloxane, a stable organosilicone compound such as dimethylpolysiloxane, which is not subjected to crosslinking reaction, may be added.

Meanwhile, examples of a degradation type physicochemical cell adhesive material include a surfactant that is degraded by photocatalytic action and has a function of changing the polarity of the surface of a photocatalyst-containing polarity-variable layer as a result of degradation. Specific examples thereof include nonionic hydrocarbon surfactants such as the NIKKOL BL, BC, BO, and BB series (Nikko Chemicals), nonionic fluorine surfactants and nonionic silicone surfactants such as ZONYL FSN and FSO (DuPont), Surflon S-141 and 145 (Asahi Glass Co., Ltd.), Megafac F-141 and 144 (Dainippon Ink and Chemicals, incorporated), Ftergent F-200 and F251 (Neos), Unidyne DS-401 and 402 (Daikin Industries, ltd.), and Fluorad FC-170 and 176 (3M). Also, cationic surfactants, anionic surfactants, and amphoteric surfactants may be used.

In addition, when a degradation type physicochemical cell adhesive material is used as described above, an additional binder component is preferably used, in general. At such time, a binder component used is not particularly limited as long as it has the main structure having a high level of binding energy such that it is not degraded by photocatalytic action described above. Specific examples thereof include polysiloxane having some or no organic substituents. Such examples can be obtained through hydrolysis or polycondensation of tetramethoxysilane, tetraethoxysilane, or the like.

Further, in this embodiment, a binder type physicochemical cell adhesive material and a degradation type physicochemical cell adhesive material may be used in combination.

In addition, a physicochemical cell adhesiveness-variable material that experiences a change in cell adhesiveness due to control of electrostatic interaction is also available. In such case, a positively charged functional group contained in the material is degraded by photocatalytic action upon energy irradiation so that the positive charge content of the material surface varies, resulting in a change in cell adhesiveness. Thus, a cell adhesiveness-variation pattern is formed. Examples of such material include poly-L-lysine.

b. Biological Cell Adhesiveness-Variable Material

As a material that has biological factors that enable cells to adhere to the surface thereof, a material capable of being adhered to by many cell species and a material capable of being adhered to selectively by a specific cell species are available. The former is, for example, collagen type I and the latter is, for example, poly-(N-p-vinylbenzyl-[O-β-D-galactopyranosyl-(1→4)-D-gluconamide]) (hereafter to be referred to as PVLA) to which liver parenchymal cells selectively adhere. In the case of PVLA, it is supposed that the material contains galactose, which is specifically recognized by liver parenchymal cells, in the structure thereof, so that selective and specific adhesion takes places between the material and the cells.

The following type of usage can be considered when such material and a photocatalyst are mixed and the thus obtained photocatalyst-containing cell adhesiveness-variable layer is used. A material to be used for a photocatalyst-containing cell adhesiveness-variable layer is prepared by mixing soluble collagen type I that is obtained by solubilizing collagen type I via an enzyme treatment with a photocatalyst made of $TiO_2$ particles or the like that have been subjected to baking and pulverization. Then, a photocatalyst-containing cell adhesiveness-variable layer is formed by applying the material for a photocatalyst-containing cell adhesiveness-variable layer onto a substrate. When the photocatalyst-containing cell adhesiveness-variable layer is irradiated with a small amount of energy, the structure of a cell adhesion peptide on the side chain of the collagen is partially destroyed so that the level of cell adhesiveness can be reduced. In addition, the structure of a cell adhesion peptide can be gradually destroyed by increasing the amount of energy irradiation so that the level of cell adhesiveness can be further reduced.

Furthermore, the main chain structure of the collagen can be destroyed via excessive energy irradiation, resulting in complete loss of the cell adhesiveness thereof.

(2) Photocatalyst

Examples of a photocatalyst used in this embodiment include titanium dioxide ($TiO_2$), zinc oxide (ZnO), tin oxide ($SnO_2$), strontium titanate ($SrTiO_3$), tungsten oxide ($WO_3$), bismuth oxide ($Bi_2O_3$), and iron oxide ($Fe_2O_3$) that have been known as optical semiconductors. One or more members of such group can be used in combination.

In this embodiment, titanium dioxide is particularly preferably used, since it has high band gap energy and it is chemically stable, nontoxic, and readily available. Titanium dioxide is classified into anatase titanium dioxide and rutile titanium dioxide. Either thereof can be used in this embodiment; however, anatase titanium dioxide is preferable. Anatase titanium dioxide has an excitation wavelength of not more than 380 nm.

Examples of such anatase titanium dioxide include an anatase titania sol that is deflocculated with hydrochloric acid (STS-02 (average particle size: 7 nm) or ST-K01, Ishihara Sangyo Kaisha, Ltd.) and an anatase titania sol that is deflocculated with nitric acid (TA-15 (average particle size: 12 nm), Nissan Chemical Industries, Ltd.).

Preferably, the smaller photocatalyst particle size results in more effective photocatalytic reaction. The average particle size of the photocatalyst used is preferably not more than 50 nm and particularly preferably not more than 20 nm.

The photocatalyst content of the photocatalyst-containing cell adhesiveness-variable layer used in this embodiment may be set to 5% to 60% by weight and preferably to 20% to 40% by weight.

2. Substrate

A substrate used for the substrate for cell arrangement of the present invention is not particularly limited as long as it is made of a material with which a photocatalyst-containing cell adhesiveness-variable layer can be formed on the substrate surface. Such substrate can be used in any form as long as surface treatment can be carried out by exposure treatment. Specific example thereof include: inorganic materials such as metals, glasses, and silicones; and organic materials represented by plastics. Also, the form thereof is not limited. Examples thereof include flat plates, flat membranes, films, and porous membranes.

3. Cell Adhesiveness-Variation Pattern

In this embodiment, the aforementioned photocatalyst-containing cell adhesiveness-variable layer is formed on the substrate described above, and energy irradiation is carried out in a patterned manner thereon, such that a cell adhesiveness-variation pattern in which cell adhesiveness is varied is formed on the layer.

In general, such cell adhesiveness-variation pattern is formed with cell adhesiveness promoted regions having good cell adhesiveness and cell adhesiveness inhibited regions having poor cell adhesiveness. Cells are allowed to adhere to the cell adhesiveness promoted regions, resulting in cell adhesion in a extremely fine pattern. Such cell adhesiveness promoted regions and cell adhesiveness inhibited regions are determined depending on the types of cell adhesiveness-variable materials used.

For instance, in the case of a physicochemical cell adhesiveness-variable material that experiences a change in cell adhesiveness depending on a change in surface free energy, good cell adhesiveness is obtained when the level of surface free energy is within a certain range, and cell adhesiveness tends to deteriorate when the level of surface free energy is not within such range. As an example of a cell adhesiveness change corresponding to surface free energy, experimental results as shown in "*Biomaterial no Saisentan*" (Development of Biomaterials) edited by Yoshito Ikada, at the bottom of p. 109 (CMC Publishing Co., Ltd.) are known.

In addition, cell adhesiveness can be determined not only by the surface free energy of the material described above but also by the type of the material and the type of cells that are allowed to adhere to the material, for example.

Herein, the cell adhesiveness-variation pattern has the aforementioned cell adhesiveness promoted regions and cell adhesiveness inhibited regions. Depending on usage, such pattern may contain regions having three or more different levels of cell adhesiveness on the surface on the material.

For instance, when a photocatalyst-containing cell adhesiveness-variable layer made of a biological cell adhesiveness-variable material is used and good cell adhesiveness has not been confirmed, it is advantageous in that the optimal conditions in terms of cell adhesiveness can be found by allowing the surface conditions of the photocatalyst-containing cell adhesiveness-variable layer to continuously vary.

As described above, in accordance with the present invention, the expression "three or more levels" indicates a condition in which cell adhesiveness is continuously varied. The level is adequately determined depending on situations.

When regions having a plurality of different levels of cell adhesiveness are formed, such regions can be formed by changing the amount of energy irradiation provided to the photocatalyst-containing cell adhesiveness-variable layer. Specifically, a method wherein overlapping exposure is carried out more than once using halftone photomasks that have different transmittances or a plurality of photomasks that have different patterns of light shielding parts can be employed.

Further, in this embodiment, cell adhesiveness-variation patterns in which there are differences of photocatalytic activity between areas subjected to energy irradiation and areas not subjected to energy irradiation can be used. Specifically, a biological cell adhesiveness-variable material that is introduced into a photocatalyst-containing cell adhesiveness-variable layer can be used as a substance to be degraded. In such case, when the surface of the photocatalyst-containing cell adhesiveness-variable layer is subjected to energy irradiation in a patterned manner, the biological cell adhesiveness-variable material that is exuded on the irradiated surface is degraded in areas subjected to irradiation, and a biological cell adhesiveness-variable material remains in areas not subjected to energy irradiation. Accordingly, when the biological cell adhesiveness-variable material has good cell adhesiveness with respect to certain cells or to many other cells, an area not subjected to energy irradiation is determined to be a cell adhesiveness promoted region. On the other hand, an area subjected to energy irradiation is determined to be a region in which a biological cell adhesiveness-variable material having good cell adhesiveness does not exist and a photocatalyst that is activated via energy irradiation so as to have disinfection properties is exposed. Therefore, when the area subjected to energy irradiation is determined to be a cell adhesiveness inhibited region, the substrate for cell arrangement of this embodiment is advantageous in that the pattern width does not become excessive after cell culture for a certain period of time.

B. Second Embodiment

In the second embodiment, the substrate for cell arrangement of the present invention has a substrate and a cell adhesiveness-variable layer, which is formed on the substrate and contains a cell adhesiveness-variable material that experiences a change in cell adhesiveness due to photocatalytic action upon energy irradiation. In addition, a cell adhesiveness-variation pattern in which cell adhesiveness is varied is formed on the cell adhesiveness-variable layer. The substrate for cell arrangement is characterized in that the cell adhesiveness-variable layer contains a photocatalyst treatment layer containing a photocatalyst and a cell adhesiveness-variable material layer that is formed on the photocatalyst treatment layer and contains the cell adhesiveness-variable material.

In this embodiment, the cell adhesiveness-variable layer has a photocatalyst treatment layer formed on the substrate and a cell adhesiveness-variable material layer formed on the photocatalyst treatment layer. Thus, upon energy irradiation, cell adhesiveness of the cell adhesiveness-variable material in a cell adhesiveness-variable material layer is varied due to the action of a photocatalyst in a photocatalyst treatment layer. Therefore, a cell adhesiveness-variation pattern can be formed, in which cell adhesiveness differs between areas subjected to energy irradiation and areas not subjected to energy irradiation.

Each member used in the substrate for cell arrangement of the above embodiment will be independently described.

1. Cell Adhesiveness-Variable Material Layer

In the case of the substrate for cell arrangement of this embodiment, a cell adhesiveness-variable material layer is formed on a photocatalyst treatment layer that is formed on a substrate. Such cell adhesiveness-variable material layer can be formed using the cell adhesiveness-variable material described in the above first embodiment. Hereafter, a cell adhesiveness-variable material layer made of a physicochemical cell adhesiveness-variable material and a cell adhesiveness-variable material layer made of a biological cell adhesiveness-variable material will be independently described.

(1) Use of a Physicochemical Cell Adhesiveness-Variable Material

In this embodiment, the cell adhesiveness-variable material layer made of a physicochemical cell adhesiveness-variable material may be a layer made of a material similar to that described in the above first embodiment. When using such material, the layer is similar to that described above except for a difference in terms of the presence or absence of a photocatalyst. In addition, in this embodiment, the cell adhesiveness-variable material layer does not essentially need to contain a photocatalyst; however, it may contain a small amount of a photocatalyst in view of sensitivity or the like.

Further, in this embodiment, a cell adhesiveness-variable material layer that serves as a layer to be removed via degradation induced by photocatalytic action is formed on a photocatalyst treatment layer. Then, regions in which a cell adhesiveness-variable material layer is degraded via photocatalytic action upon energy irradiation (i.e., regions in which a photocatalyst treatment layer is exposed) and regions in which a cell adhesiveness-variable material layer remains are formed. As a result, a cell adhesiveness-variable material layer that may be used contains the thus obtained cell adhesiveness-variation pattern.

Specifically, when cell adhesiveness is controlled based on surface free energy, a physicochemical cell adhesiveness-variable material having surface free energy that is appropriate for cell adhesiveness is used, a cell adhesiveness-variable material layer is formed by applying the material to the entirety of the surface of a photocatalyst treatment layer, and patterned energy irradiation is carried out, so that a pattern in which the cell adhesiveness-variable material layer partially remains is formed. Thus, a cell adhesiveness-variation pattern can be obtained.

Examples of a material that can be used when cell adhesiveness is controlled based on surface free energy include regenerated cellulose and nylon 11. The material is used in the physicochemical cell adhesiveness-variable material layer serving as a layer to be removed via degradation.

Also, when cell adhesiveness is controlled based on electrostatic interaction, a positively charged physicochemical cell adhesiveness-variable material is used so that a cell adhesiveness-variation pattern can be obtained by a method as described above.

Examples of a material that can be used when cell adhesiveness is controlled based on electrostatic interaction include polyamine-graft poly(2-hydroxymethyl-methacrylate) (HA-x). The material is used in the physicochemical cell adhesiveness-variable material layer serving as a layer to be removed via degradation.

Such resin is allowed to dissolve in a solvent, and the layer to be removed via degradation can be formed by a general film-forming method such as spin coating. In addition, in the present invention, it is possible to form a defect-free film with the use of functional thin films such as a self-assembled monolayer, a Langmuir-Blodgett film, and a layer-by-layer self-assembly film. Thus, it can be preferable to use such film-forming method.

When a cell adhesiveness-variation pattern is formed using a cell adhesiveness-variable material layer serving as a layer to be removed via degradation, since a photocatalyst treatment layer described below is exposed in a region removed via degradation, cell culture is significantly inhibited in such region. Thus, a substrate for cell arrangement obtained via such method is advantageous in that an extremely fine pattern can be maintained after a long period of time for cell retention.

(2) Use of a Biological Cell Adhesiveness-Variable Material

In this embodiment, a cell adhesiveness-variable material layer made of a biological cell adhesiveness-variable material that can be used is similar to that described in the first embodiment. Examples of the material include collagen type I.

2. Photocatalyst Treatment Layer

Next, the photocatalyst treatment layer used in the present invention will be described. The photocatalyst treatment layer used in the present invention is not particularly limited as long as it is structured such that a photocatalyst in a photocatalyst treatment layer causes a change in cell adhesion properties of the cell adhesiveness-variable material layer that is formed on the photocatalyst treatment layer. The photocatalyst treatment layer may be formed with a photocatalyst and a binder or may consist of a photocatalyst. In addition, the surface properties of the photocatalyst treatment layer may be lyophilicity or lyophobicity. Since a cell adhesiveness-variable material layer and the like are formed on the photocatalyst treatment layer, the photocatalyst treatment layer is preferably lyophilic.

The action mechanism of a photocatalyst represented by titanium oxide described below in the photocatalyst treatment layer is not completely clear. It is considered that carriers generated upon light irradiation cause a change in the chemical structure of organic matter due to direct reaction with a neighboring compound or due to reactive oxygen species generated in the presence of oxygen and water. In the present invention, such carriers are considered to act on a compound in the cell adhesiveness-variable material layer formed on the photocatalyst treatment layer. Such photocatalyst is similar to that described in detail in the first embodiment.

The photocatalyst treatment layer in this embodiment may consist of a photocatalyst as described above or it may be formed by mixing a photocatalyst with a binder.

In the case of a photocatalyst treatment layer consisting of a photocatalyst, the efficiency relative to a change in the cell adhesion properties of the cell adhesiveness-variable material layer is improved, resulting in an advantage in terms of cost due to shortened treatment time or the like. Meanwhile, in the case of a photocatalyst treatment layer comprising a photocatalyst and a binder, there is an advantage in that the photocatalyst treatment layer is readily formed.

Examples of a method for forming a photocatalyst treatment layer consisting of a photocatalyst include a sputtering method, a CVD method, and vacuum deposition methods such as a vacuum evaporation method. When the photocatalyst treatment layer is formed by vacuum deposition methods, it is possible to obtain a photocatalyst treatment layer that is a uniformly formed film and consists of a photocatalyst. Thus, it becomes possible to uniformly change properties of the cell adhesiveness-variable material layer. In addition, since the photocatalyst treatment layer consists of a photocatalyst, it becomes possible to efficiently change cell adhesiveness of the cell adhesiveness-variable layer, compared with a case in which a binder is used.

Other examples of a method for forming the photocatalyst treatment layer consisting of a photocatalyst include a method wherein amorphous titania is formed on a substrate and crystalline titania is obtained as a result of phase change via baking when the photocatalyst is titanium dioxide or the like. Amorphous titania used herein can be obtained via hydrolysis and dehydration condensation, in the presence of acids, of inorganic salts of titanium such as titanium tetrachloride and titanium sulfate or via hydrolysis and dehydration condensation of organic titanium compounds such as tetraethoxytitanium, tetraisopropoxytitanium, tetra-n-propoxytitanium, tetrabutoxytitanium, and tetramethoxytitanium. Then, the thus obtained amorphous titania can be modified to anatase titania and rutile titania via baking at 400° C. to 500° C. and at 600° C. to 700° C., respectively.

When a binder is used, a binder preferably has the main structure having a high level of binding energy such that it is not degraded via the aforementioned photocatalytic action. Examples of such binder include organopolysiloxane described above.

As described above, when organopolysiloxane is used as a binder, the photocatalyst treatment layer can be formed in a manner such that a photocatalyst and organopolysiloxane as a binder are allowed to be dispersed in a solvent with other additives according to need so as to prepare an applied liquid, and the liquid is then applied to a transparent substrate. Examples of the solvent used include alcoholic organic solvents such as ethanol and isopropanol. Such solvent can be applied via known coating methods such as spin coating, spray coating, dip coating, roll coating, and bead coating. When such solvent contains a UV-curable component as a binder, the photocatalyst treatment layer can be formed via curing treatment with UV irradiation.

Also, an amorphous silica precursor may be used as a binder. Such amorphous silica precursor is represented by the following general formula: $SiX_4$. In the formula, preferably, such amorphous precursor is a silicon compound in which X is halogen, methoxy, ethoxy, acetyl, or the like, silanol, which is a hydrolysate of the compound, or polysiloxane having an average molecular weight of not more than 3000.

Specific examples thereof include tetraethoxysilane, tetraisopropoxysilane, tetra-n-propoxysilane, tetrabutoxysilane, and tetramethoxysilane. In such case, the photocatalyst treatment layer can be formed in a manner such that an amorphous silica precursor and photocatalyst particles are allowed to be uniformly dispersed in an nonaqueous solvent and the resultant is hydrolyzed with moisture in the air on a transparent substrate so as to form silanol, followed by dehydration condensation polymerization at a room temperature. When silanol is subjected to dehydration condensation polymerization at not less than 100° C., the polymerization degree of silanol increases such that the strength of the film surface can be improved. In addition, such binders can be used alone, or two or more thereof can be used in combination.

The photocatalyst content in the photocatalyst treatment layer when a binder is used can be set to 5% to 60% by weight and preferably to 20% to 40% by weight. In addition, the thickness of the photocatalyst treatment layer is preferably 0.05 to 10 μm.

Further, the photocatalyst treatment layer may contain a surfactant in addition to a photocatalyst and a binder described above. Specific examples of such surfactant include nonionic hydrocarbon surfactants such as the NIKKOL BL, BC, BO, and BB series (Nikko Chemicals), nonionic fluorine surfactants and and nonionic silicone surfactants such as ZONYL FSN and FSO (DuPont), Surflon S-141 and 145 (Asahi Glass Co., Ltd.), Megafac F-141 and 144 (Dainippon Ink and Chemicals, incorporated), Ftergent F-200 and F251 (Neos), Unidyne DS-401 and 402 (Daikin Industries, ltd.), and Fluorad FC-170 and 176 (3M). Also, cationic surfactants, anionic surfactants, and amphoteric surfactants may be used.

Furthermore, in addition to the aforementioned surfactant, the photocatalyst treatment layer may contain oligomers or polymers of polyvinyl alcohol, unsaturated polyester, acryl resin, polyethylene, diallylphthalate, ethylene propylene diene monomer, epoxy resin, phenol resin, polyurethane, melamine resin, polycarbonate, polyvinyl chloride, polyamide, polyimide, styrene-butadiene-rubber, chloroprene-rubber, polypropylene, polybutylene, polystyrene, polyvinyl acetate, polyester, polybutadiene, polybenzimidazole, polyacrylonitrile, epichlorohydrin, polysulfide, polyisoprene, or the like.

3. Substrate

A substrate used in this embodiment is not particularly limited as long as the aforementioned photocatalyst treatment layer can be formed thereon. A substrate similar to that described in the first embodiment can be used.

4. Cell Adhesiveness-Variation Pattern

In this embodiment, a cell adhesiveness-variation pattern is formed in a manner such that the aforementioned cell adhesiveness-variable material layer is subjected to energy irradiation in a patterned manner such that cell adhesiveness on the surface of the cell adhesiveness-variable material layer is varied due to the action of a photocatalyst in the photocatalyst treatment layer.

C. Third Embodiment

In this embodiment, the substrate for cell arrangement of the present invention has a substrate and a cell adhesiveness-variable layer which is formed on the substrate and contains a cell adhesiveness-variable material that experiences a change in cell adhesiveness due to photocatalytic action upon energy irradiation. In addition, a cell adhesiveness-variation pattern in which cell adhesiveness is varied is formed on the cell adhesiveness-variable layer. The substrate is characterized in that the cell adhesiveness-variable layer is a cell adhesiveness-variable material layer that contains the cell adhesiveness-variable material and the cell adhesiveness variable pattern is formed via energy irradiation from a certain direction after a photocatalyst treatment layer containing a photocatalyst and the cell adhesiveness-variable material layer are placed in a manner such that they are opposed to each other.

In this embodiment, the cell adhesiveness-variable layer is a cell adhesiveness-variable material layer as described above and the aforementioned cell adhesiveness variable pattern is formed via energy irradiation from a certain direction after a photocatalyst treatment layer containing a photocatalyst and the cell adhesiveness-variable material layer are placed in a manner such that they are opposed to each other. Thus, upon energy irradiation, cell adhesiveness of the cell adhesiveness-variable material in the cell adhesiveness-variable material layer is varied due to the action of a photocatalyst in the photocatalyst-containing layer such that a cell adhesiveness-variation pattern in which cell adhesiveness differs between areas subjected to energy irradiation and areas not subjected to energy irradiation can be formed.

Each member used in the substrate for cell arrangement in this embodiment will be independently described below.

1. Cell Adhesiveness-Variable Material Layer

In the case of the substrate for cell arrangement of this embodiment, a cell adhesiveness-variable material layer is formed on a substrate. The cell adhesiveness-variable material layer is similar to that formed by using the material described in the above second embodiment. In addition, in this embodiment, the cell adhesiveness-variable material layer does not essentially need to contain a photocatalyst; however, a small amount of photocatalyst may be contained in view of sensitivity or the like.

In addition, in this embodiment, a cell adhesiveness-variable material layer as a layer to be removed via degradation induced by photocatalytic action may be formed on the substrate as described in the above second embodiment. In such case, the cell adhesiveness-variable material layer used has a cell adhesiveness-variation pattern obtained by forming regions in which the cell adhesiveness-variable material layer is degraded via photocatalytic action upon energy irradiation using a photocatalyst-containing layer-side basal plate (i.e., regions in which the substrate is exposed) and regions in which the cell adhesiveness-variable material layer remains.

2. Substrate

The substrate used in this embodiment is not particularly limited as long as the aforementioned cell adhesiveness-variable material layer can be formed. Such substrate that can be used is similar to that described in the first embodiment.

3. Photocatalyst-Containing Layer

Next, the photocatalyst-containing layer used in this embodiment will be described. The photocatalyst-containing layer used in this embodiment is formed on a substrate made of glass or the like so as to be used, in general. In this embodiment, such photocatalyst-containing layer is placed so as to be opposed to the aforementioned cell adhesiveness-variable material layer, followed by energy irradiation. Thus, cell adhesiveness of the cell adhesiveness-variable material layer is allowed to vary due to the action of a photocatalyst contained in the photocatalyst-containing layer. In this embodiment, the photocatalyst-containing layer is placed at a certain position upon energy irradiation such that a cell adhesiveness-variation pattern can be formed. Thus, the aforementioned cell adhesiveness-variable material layer does not necessarily contain a photocatalyst. Therefore, it is advantageous in that a photocatalyst does not affect the cell adhesiveness-variable material layer in a time-dependent manner.

Such photocatalyst-containing layer is similar to that described in the second embodiment in connection with a photocatalyst treatment layer.

4. Cell Adhesiveness-Variation Pattern

In this embodiment, a cell adhesiveness-variation pattern is formed in a manner such that the aforementioned cell adhesiveness-variable material layer is subjected to energy irradiation in a patterned manner using the photocatalyst-containing layer such that cell adhesiveness on the surface of the cell adhesiveness-variable material layer is varied due to the action of a photocatalyst in the photocatalyst-containing layer.

II. Method for Producing a Substrate for Cell Arrangement

Next, the method for producing a substrate for cell arrangement of the present invention will be described. For instance, in the three embodiments of the method for producing a substrate for cell arrangement of the present invention described above, the method is characterized in that: a substrate for pattern formation is formed, which has a substrate and a layer; the layer is formed on the substrate and experiences a change in cell adhesiveness due to photocatalytic action upon energy irradiation; the substrate for pattern formation is subjected to energy irradiation so as to activate a photocatalyst; and a cell adhesiveness-variation pattern on which cell adhesiveness is varied is formed.

In accordance with the method for producing a substrate for cell arrangement of the present invention, the layer that experiences a change in cell adhesiveness due to photocatalytic action upon energy irradiation is formed. Thus, when such layer is subjected to energy irradiation in a required pattern, it is possible to readily produce a substrate for cell arrangement in which cell adhesiveness is varied in an extremely fine cell adhesiveness-variation pattern. Thus, without using a treatment liquid that adversely affects cells, a substrate for cell arrangement forming such extremely fine pattern can be produced by simple steps. In addition, since there is no need to modify the cell adhesiveness-variable material, it is possible to broaden the options of such material. Thus, a biological cell adhesiveness-variable material as described below, which exerts specific cell adhesiveness, can be used without problems.

Hereafter, the method for producing a substrate for cell arrangement of the present invention will be described in connection with embodiments 1 to 3 above.

A. First Embodiment

First, the first embodiment of the substrate for cell arrangement of the present invention will be described. In the first embodiment, the method for producing a substrate for cell arrangement of the present invention comprises the steps of:

forming a substrate for pattern formation in a manner such that a substrate for pattern formation has a substrate and a photocatalyst-containing cell adhesiveness-variable layer that is formed on the substrate and has a photocatalyst and a cell adhesiveness-variable material that experiences a change in cell adhesiveness due to photocatalytic action upon energy irradiation; and forming a cell adhesiveness-variation pattern in a manner such that the photocatalyst-containing cell adhesiveness-variable layer is subjected to energy irradiation, resulting in a change in the cell adhesiveness thereof.

Figure 4:
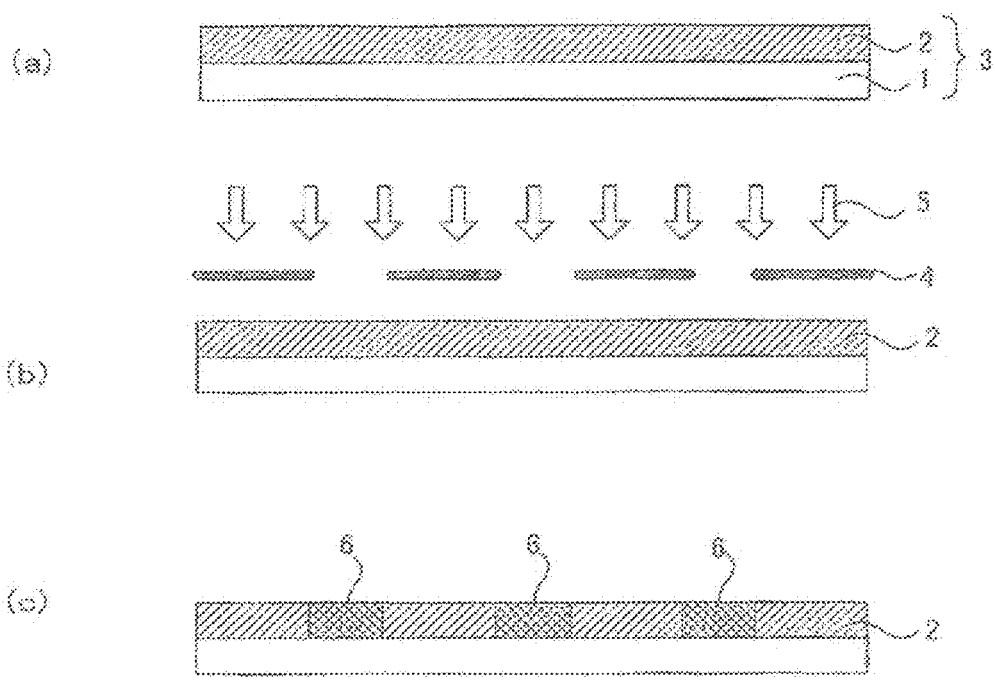
FIG. 4 shows a process chart of an example of a method for producing a substrate for cell arrangement of the present invention.

In accordance with the method for producing a substrate for cell arrangement of this embodiment, as shown in FIG. 4, for example, a substrate for pattern formation 3 is formed, which has a substrate 1 and a photocatalyst-containing cell adhesiveness-variable layer 2 that is formed on the substrate 1 (a step of forming a substrate for pattern formation (FIG. 4 (*a*))). Then, a step of forming a cell adhesiveness-variation pattern is carried out in a manner such that the photocatalyst-containing cell adhesiveness-variable layer 2 is irradiated with energy 5 using, for example, a photomask 4 (FIG. 4 (*b*)), and thus a cell adhesiveness-variation pattern 6 is formed, on which cell adhesiveness of the photocatalyst-containing cell adhesiveness-variable layer 2 is varied (FIG. 4 (*c*)).

In this embodiment, a photocatalyst-containing cell adhesiveness-variable layer that has a photocatalyst and the cell adhesiveness-variable material is formed. Thus, in the step of forming a cell adhesiveness-variation pattern, cell adhesiveness of the cell adhesiveness-variable material is varied due to the action of a photocatalyst in the photocatalyst-containing cell adhesiveness-variable layer upon energy irradiation such that it becomes possible to form a cell adhesiveness-variation pattern on which areas subjected to energy irradiation and areas not subjected to energy irradiation differ in terms of cell adhesiveness. Hereafter, each step of this embodiment will be described.

1. Step of Forming a Substrate for Pattern Formation

First, the step of forming a substrate for pattern formation of this embodiment will be described. In the step of forming a substrate for pattern formation of this embodiment, a substrate for pattern formation is formed, having a substrate and a photocatalyst-containing cell adhesiveness-variable layer that is formed on the substrate and has a photocatalyst and a cell adhesiveness-variable material that experiences a change in cell adhesiveness due to photocatalytic action upon energy irradiation.

The step can be carried out by applying a coating liquid containing a photocatalyst and a cell adhesiveness-variable material to a substrate via known coating methods such as spin coating, spray coating, dip coating, roll coating, and bead coating so as to form a photocatalyst-containing cell adhesiveness-variable layer. When the coating liquid contains a UV-curable component that serves as a binder, a photocatalyst-containing layer can be formed via curing treatment with UV irradiation.

2. Step of Forming a Cell Adhesiveness-Variation Pattern

Next, the step of forming a cell adhesiveness-variation pattern of this embodiment will be described. In the step of forming a cell adhesiveness-variation pattern of this embodiment, the photocatalyst-containing cell adhesiveness-variable layer is subjected to energy irradiation such that a cell adhesiveness-variation pattern on which cell adhesiveness of the photocatalyst-containing cell adhesiveness-variable layer is varied is formed.

With this step, when energy irradiation is carried out in a desired pattern, cell adhesiveness of the photocatalyst-containing cell adhesiveness-variable layer can vary only in the regions subjected to energy irradiation. Thus, an extremely fine cell adhesiveness-variation pattern containing good cell adhesiveness regions and poor cell adhesiveness regions can be formed.

The term "energy irradiation (exposure)" used in this embodiment indicates a concept that includes irradiation by any form of energy ray that can cause a change in cell adhesiveness of the surface of a photocatalyst-containing cell adhesiveness-variable layer. Thus, such irradiation is not limited to visible light irradiation.

In general, the wavelength of light used for such energy irradiation is set to not more than 400 nm and preferably not more than 380 nm. This is because, as described above, a preferred example of the photocatalyst used in the photocatalyst-containing cell adhesiveness-variable layer is titanium dioxide and light having the aforementioned wavelength is preferably used as energy that can activate the photocatalytic action of titanium dioxide.

Examples of a light source that can be used for such energy irradiation include a mercury lamp, a metal halide lamp, a xenon lamp, an excimer lamp, and other various types of light sources.

In addition to a method for carrying out patterned irradiation via a photomask using the light source described above, it is possible to use a method for carrying out lithography irradiation in a pattern using an excimer or YAG laser, for example.

Further, upon energy irradiation, the amount of energy irradiation is determined to be equivalent to the amount of irradiation that is required to cause a change in cell adhesiveness of the surface of a photocatalyst-containing cell adhesiveness-variable layer due to the action of a photocatalyst in the photocatalyst-containing cell adhesiveness-variable layer.

Since cell adhesiveness of the surface of a photocatalyst-containing cell adhesiveness-variable layer is varied depending on the amount of energy irradiation, it is possible to control cell adhesiveness by controlling the period of time of energy irradiation, for example. Accordingly, adequate cell adhesiveness can be imparted to the surface. As described above, cell adhesiveness can be evaluated based on surface water contact angle. Thus, adequate cell adhesiveness can be imparted to the surface by controlling the period of time of energy irradiation in a manner such that the surface can achieve an adequate water contact angle. For instance, when fluoroalkylsilane is used as a cell adhesiveness-variable material and UV irradiation at 365 nm is carried out at an intensity of 25.0 mW/second, a surface having adequate adhesiveness can be obtained via irradiation for generally 120 to 600 seconds and preferably 240 to 480 seconds in a case where quartz is used in a substrate of a photomask. The period of time of energy irradiation, the irradiation intensity, and the like can be appropriately controlled depending on the material used in the substrate, the cell adhesiveness-variable material used, and the like.

At such time, it becomes possible to increase sensitivity via energy irradiation while heating a photocatalyst-containing cell adhesiveness-variable layer. Thus, such heating is preferable because it efficiently allows cell adhesiveness to be varied. Specifically, a photocatalyst-containing cell adhesiveness-variable layer is preferably heated at 30° C. to 80° C.

With regard to the direction of energy irradiation of this embodiment, in a case where the aforementioned substrate is transparent, patterned energy irradiation via a photomask or lithography irradiation using a laser may be carried out from either the substrate side or the photocatalyst-containing cell adhesiveness-variable layer side. Meanwhile, in a case where the substrate is not transparent, it is necessary to carry out energy irradiation from the photocatalyst-containing cell adhesiveness-variable layer side.

B. Second Embodiment

Next, the second embodiment of the method for producing a substrate for cell arrangement of the present invention will be described. In the second embodiment, the method for producing a substrate for cell arrangement of the present invention comprises the steps of:

forming a substrate for pattern formation in a manner such that the substrate for pattern formation has a substrate, a photocatalyst-containing photocatalyst treatment layer formed on the substrate, and a cell adhesiveness-variable material layer that is formed on the photocatalyst treatment layer and has a cell adhesiveness-variable material that experiences a change in cell adhesiveness due to photocatalytic action upon energy irradiation; and forming a cell adhesiveness-variation pattern in a manner such that the cell adhesiveness-variable material layer is subjected to energy irradiation, resulting in a change in the cell adhesiveness thereof.

Figure 5:
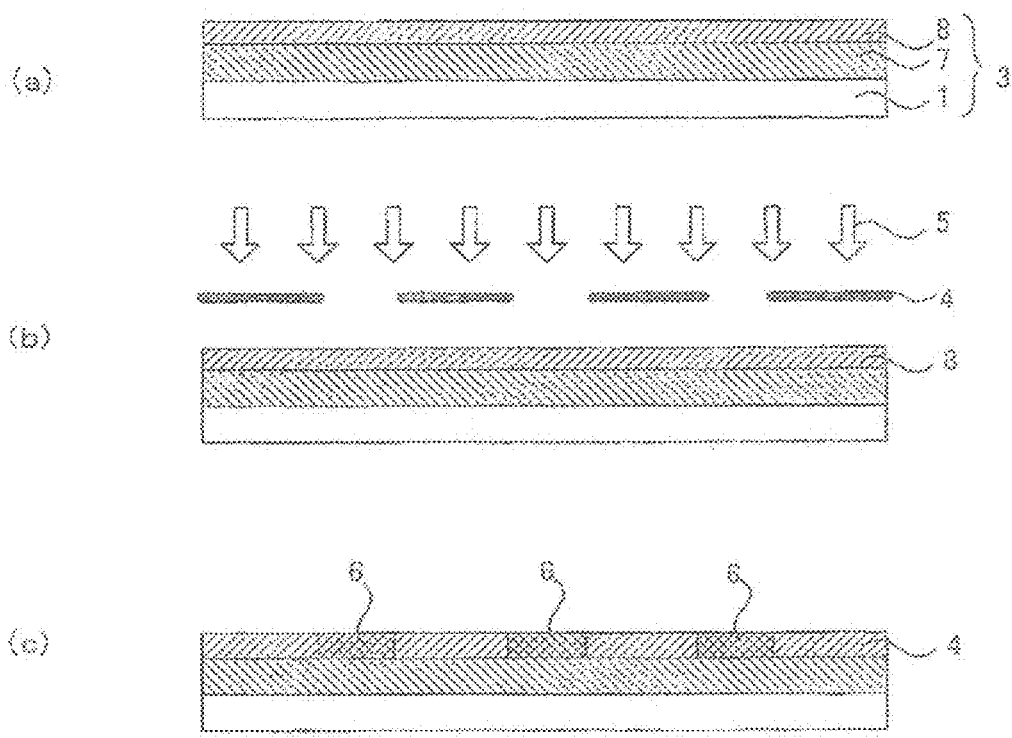
FIG. 5 shows a process chart of another example of a method for producing a substrate for cell arrangement of the present invention.

In accordance with the method for producing a substrate for cell arrangement of this embodiment, as shown in FIG. 5, for example, a substrate for pattern formation 3 that has a substrate 1, a photocatalyst treatment layer 7 formed on the substrate 1, and a cell adhesiveness-variable material layer 8 formed on the photocatalyst treatment layer 7 is formed (a step of forming a substrate for pattern formation (FIG. 5 (a))). Then, the cell adhesiveness-variable layer 8 is irradiated with energy 5 using, for example, a photomask 4 (FIG. 5 (b)) such that a cell adhesiveness-variation pattern 6 on which cell adhesiveness of the photocatalyst-containing cell adhesiveness-variable layer 8 is varied is formed (FIG. 5 (c)). As described above, the step of a cell adhesiveness-variation pattern is carried out.

In this embodiment, a photocatalyst treatment layer and the cell adhesiveness-variable material layer are formed. Thus, in the step of forming a cell adhesiveness-variation pattern, cell adhesiveness of the cell adhesiveness-variable material layer is varied due to the action of a photocatalyst in the photocatalyst treatment layer upon energy irradiation such that a cell adhesiveness-variation pattern on which areas subjected to energy irradiation and areas subjected to no energy irradiation differ in terms of cell adhesiveness can be formed. Hereafter, each step of this embodiment will be described.

1. Step of Forming a Substrate for Pattern Formation

First, the step of forming a substrate for pattern formation of this embodiment will be described. In the step of forming a substrate for pattern formation of this embodiment, a substrate for pattern formation is formed, which has a photocatalyst-containing photocatalyst treatment layer formed on the substrate and a cell adhesiveness-variable material layer that is formed on the photocatalyst treatment layer and has a cell adhesiveness-variable material that experiences a change in cell adhesiveness due to photocatalytic action upon energy irradiation.

The photocatalyst treatment layer formed in this step may consist of a photocatalyst or may be formed by mixing a photocatalyst with a binder.

Examples of a method for forming a photocatalyst treatment layer consisting of a photocatalyst include a sputtering method, a CVD method, and vacuum deposition methods such as a vacuum evaporation method. When the photocatalyst used is titanium dioxide or the like, a method wherein amorphous titania is formed on a substrate so as to be subjected to baking such that crystalline titania is obtained through phase change can be used. When a photocatalyst treatment layer is formed by a vacuum deposition method, it is possible to obtain a photocatalyst treatment layer that is a uniformly formed membrane and consists of a photocatalyst alone. Thus, it becomes possible to uniformly cause a change in the cell adhesiveness of the cell adhesiveness-variable material layer. In addition, since such photocatalyst treatment layer consists of a photocatalyst, it becomes possible to efficiently cause a change in the cell adhesiveness of the cell adhesiveness-variable layer, compared with the case in which a binder is used.

In addition, when a photocatalyst treatment layer is formed by mixing a photocatalyst and a binder, a photocatalyst treatment layer can be formed in a manner such that an applied liquid is prepared by dispersing a photocatalyst and a binder in a solvent with other additives according to need, and following which the applied liquid is applied to a transparent substrate. Preferred examples of the solvent used include alcoholic organic solvents such as ethanol and isopropanol. Such solvent can be applied via known coating methods such as spin coating, spray coating, dip coating, roll coating, and bead coating. When a UV-curable component is contained in a solvent as a binder, the photocatalyst treatment layer can be formed via curing treatment with UV irradiation.

Next, a cell adhesiveness-variable material layer can be formed by applying the aforementioned a coating liquid containing a cell adhesiveness-variable material to the photocatalyst treatment layer via known coating methods such as spin coating, spray coating, dip coating, roll coating, and bead coating. When a UV-curable component is contained in a solvent as a binder, the photocatalyst treatment layer can be formed via curing treatment with UV irradiation.

Herein, the substrate, the photocatalyst treatment layer, and the cell adhesiveness-variable material layer that are used in this step are similar to those described in the aforementioned second embodiment, "I. Substrate for cell arrangement."

2. Step of Forming a Cell Adhesiveness-Variation Pattern

Next, a step of forming a cell adhesiveness-variation pattern of this embodiment will be described. In the step of forming a cell adhesiveness-variation pattern of this embodiment, the cell adhesiveness-variable material layer is subjected to energy irradiation so that the cell adhesiveness of the cell adhesiveness-variable material layer is varied, resulting in the formation of a cell adhesiveness-variation pattern.

In this step, energy irradiation is carried out in a desired pattern such that cell adhesiveness of the cell adhesiveness-variable material layer can vary exclusively in regions subjected to energy irradiation. Thus, an extremely fine cell adhesiveness-variation pattern containing good cell adhesiveness regions and poor cell adhesiveness regions can be formed.

The energy irradiation method, irradiation energy, and the amount of energy irradiation in this step are similar to those in the first embodiment described above.

C. Third Embodiment

Next, the third embodiment of the substrate for cell arrangement of the present invention will be described. In the third embodiment, the method for producing a substrate for cell arrangement comprises the steps of:

forming a substrate for pattern formation in a manner such that the substrate for pattern formation has a substrate and a cell adhesiveness-variable material layer that is formed on the substrate and contains a cell adhesiveness-variable material that experiences a change in cell adhesiveness due to photocatalytic action upon energy irradiation; and forming a cell adhesiveness-variation pattern in a manner such that, after the substrate for pattern formation and a photocatalyst-containing layer-side basal plate that contains a photocatalyst-containing layer and a base body are placed such that the cell adhesiveness-variable material layer and the photocatalyst-containing layer are opposed to each other, energy irradiation is carried out from a certain direction such that the cell adhesiveness-variation pattern is formed, resulting in variation of the cell adhesiveness of the cell adhesiveness-variable material layer.

Figure 6:
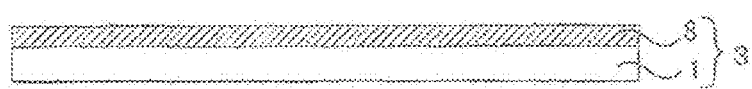
FIG. 6 shows a process chart of another example of a method for producing a substrate for cell arrangement of the present invention.
Figure 6:
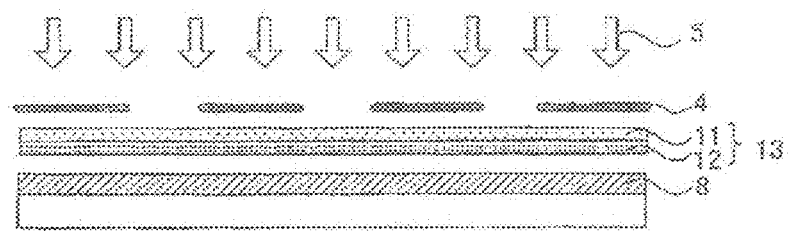
Figure 6:
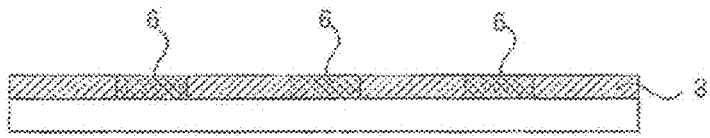

In accordance with the method for producing a substrate for cell arrangement of this embodiment, as shown in FIG. 6, for example, a substrate for pattern formation 3 that has a substrate 1 and a cell adhesiveness-variable material layer 8 formed on the substrate 1 is formed (a step of forming a substrate for pattern formation (FIG. 6 (a))). Thereafter, a photocatalyst-containing layer-side basal plate 13 that has a base body 11 and a photocatalyst-containing layer 12 formed on the base body 11 is prepared. Then, the photocatalyst-containing layer 12 of the photocatalyst-containing layer-side basal plate 13 and the cell adhesiveness-variable layer 8 are placed such that they are opposed to each other, followed by irradiation of energy 5 using, for example, a photomask 4 (FIG. 6 (b)). Thereafter, a cell adhesiveness-variation pattern 6 is formed, on which cell adhesiveness of the cell adhesiveness-variable layer 8 is varied (FIG. 6 (c)). As described above, the step of forming a cell adhesiveness-variation pattern is carried out.

In this embodiment, a cell adhesiveness-variable material layer is formed. Thus, in the step of forming a cell adhesiveness-variation pattern, energy irradiation is carried out using a photocatalyst-containing layer-side basal plate such that cell adhesiveness of the cell adhesiveness-variable material layer is varied due to the action of a photocatalyst in the photocatalyst-containing layer. Accordingly, a cell adhesiveness-variation pattern can be formed, on which areas subjected to energy irradiation and areas not subjected to energy irradiation differ in terms of cell adhesiveness. Hereafter, each step of this embodiment will be described.

1. Step of Forming a Substrate for Pattern Formation

First, the step of forming a substrate for pattern formation of the present invention will be described. In the step of forming a substrate for pattern formation of the present invention, a substrate for pattern formation is formed, which has a substrate and a cell adhesiveness-variable material layer that is formed on the substrate and contains a cell adhesiveness-variable material that experiences a change in cell adhesiveness due to photocatalytic action upon energy irradiation.

This step can be carried out by applying a coating liquid containing a cell adhesiveness-variable material to a substrate by known coating methods such as spin coating, spray coating, dip coating, roll coating, and bead coating so as to form a cell adhesiveness-variable material layer. In addition, when the coating liquid contains a UV-curable component as a binder, a photocatalyst-containing layer can be formed by curing treatment with UV irradiation.

Herein, the substrate and the cell adhesiveness-variable material that are used in this embodiment are similar to those described in the first embodiment, "I. Substrate for cell arrangement."

2. Step of Forming a Cell Adhesiveness-Variation Pattern

Next, the step of forming a cell adhesiveness-variation pattern of this embodiment will be described. In the step of forming a cell adhesiveness-variation pattern of this embodiment, a substrate for pattern formation and a photocatalyst-containing layer-side basal plate that has a base body and a photocatalyst-containing layer that contains a photocatalyst are placed such that the cell adhesiveness-variable material layer and the photocatalyst-containing layer are opposed to each other. Then, energy irradiation is carried out from a certain direction such that a cell adhesiveness-variation pattern is formed, on which adhesiveness of the cell adhesiveness-variable material layer is varied.

In this embodiment, the photocatalyst-containing layer of the photocatalyst-containing layer-side basal plate and the cell adhesiveness-variable material layer are placed such that they are opposed to each other. Then, energy irradiation is carried out in a desired pattern such that cell adhesiveness of the cell adhesiveness-variable material layer can vary exclusively in regions subjected to energy irradiation. Thus, an extremely fine cell adhesiveness-variation pattern containing good cell adhesiveness regions and poor cell adhesiveness regions can be formed.

Hereafter, the photocatalyst-containing layer-side basal plate and energy irradiation that are used in this embodiment will be independently described.

(1) Photocatalyst-Containing Layer-Side Basal Plate

First, the photocatalyst-containing layer-side basal plate used in this embodiment will be described.

The photocatalyst-containing layer-side basal plate used in this embodiment has at least a photocatalyst-containing layer and a base body. In general, such basal plate has a thin-film photocatalyst-containing layer that is formed on a base body by a certain method. In addition, such photocatalyst-containing layer-side basal plate that can be used may have a primer layer or a photocatalyst-containing layer-side light shielding part that is formed in a pattern.

In this embodiment, upon energy irradiation, the cell adhesiveness-variable material layer and the photocatalyst-containing layer of the photocatalyst-containing layer-side basal plate are placed such that they are opposed to each other with a certain gap therebetween. Then, the cell adhesiveness of the cell adhesiveness-variable material layer is allowed to vary due to the action of the photocatalyst-containing layer of the photocatalyst-containing layer-side basal plate. After energy irradiation, the photocatalyst-containing layer-side basal plate is removed so that a cell adhesiveness-variation pattern can be formed. Hereafter, each component of the photocatalyst-containing layer-side basal plate will be described.

a. Photocatalyst-Containing Layer

The photocatalyst-containing layer used in this embodiment contains at least a photocatalyst and may or may not contain a binder. In this regard, the photocatalyst-containing layer is similar to the photocatalyst treatment layer in the aforementioned second embodiment.

Figure 7:
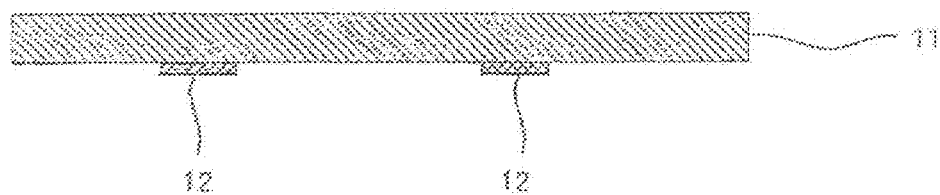
FIG. 7 shows a schematic cross-section of an example of the photocatalyst-containing layer-side basal plate of the present invention.

Herein, as shown in FIG. 6, for example, the photocatalyst-containing layer used in this embodiment may be formed on the entirety of the surface of a base body 11. Also, as shown in FIG. 7, for example, a photocatalyst-containing layer 12 may be formed in a pattern on the base body 11.

When a photocatalyst-containing layer is formed in a pattern as described above, it is not necessary to carry out patterned irradiation using a photomask or the like upon energy irradiation. The entirety of the surface of the photocatalyst-containing layer is subjected to energy irradiation such that a cell adhesiveness-variation pattern can be formed thereon.

Such method for patterning a photocatalyst-containing layer is not particularly limited. For instance, such method can be carried out using photolithography or the like.

In addition, when energy irradiation is carried out by, for example, allowing a photocatalyst-containing layer and a cell adhesiveness-variable material layer to come into close contact with each other, only areas in which a photocatalyst-containing layer has been formed experience a change in their properties. Thus, energy irradiation can be carried out from any direction for areas in which the photocatalyst-containing layer and the cell adhesiveness-variable material layer are placed such that they are opposed to each other. Further, it is an advantageous that irradiation energy is not particularly limited to parallel rays that travel in a parallel manner.

b. Base Body

In this embodiment, as shown in FIG. 6, a photocatalyst-containing layer-side basal plate 13 has at least a base body 11 and a photocatalyst-containing layer 12 formed on the base body 11. In such case, a material that constitutes the base body used is adequately selected depending on the direction of energy irradiation described below, the need for the substrate for cell arrangement of interest to be transparent, and the like.

In addition, the base body used in this embodiment may be a of material having flexibility such as a resin film or a material having no flexibility such as a glass material, for example. Further, as a base body in another form, an optical waveguide such as optical fiber can be used. These are adequately selected in accordance with energy irradiation methods.

Moreover, in order to improve the close contact between the base body surface and the photocatalyst-containing layer, an anchor layer may be formed on the base body. For instance, silane or titanium coupling agents can serve as such anchor layer.

c. Photocatalyst-Containing Layer-Side Light Shielding Part

On the photocatalyst-containing layer-side basal plate used in this embodiment, a photocatalyst-containing layer-side light shielding part may be formed in a pattern. When such photocatalyst-containing layer-side basal plate that has a photocatalyst-containing layer-side light shielding part is used, it is not necessary to use a photomask upon energy irradiation or to carry out lithography irradiation using a laser beam. Thus, since there is no need to arrange the photocatalyst-containing layer-side basal plate relative to a photomask, the steps can be simplified. In addition, an expensive apparatus that is necessary for lithography irradiation is not needed. Therefore, an advantage in terms of cost can be achieved.

Depending on the position at which a photocatalyst-containing layer-side light shielding part is formed, the following two embodiments of such photocatalyst-containing layer-side basal plate having a photocatalyst-containing layer-side light shielding part can be obtained.

Figure 8:
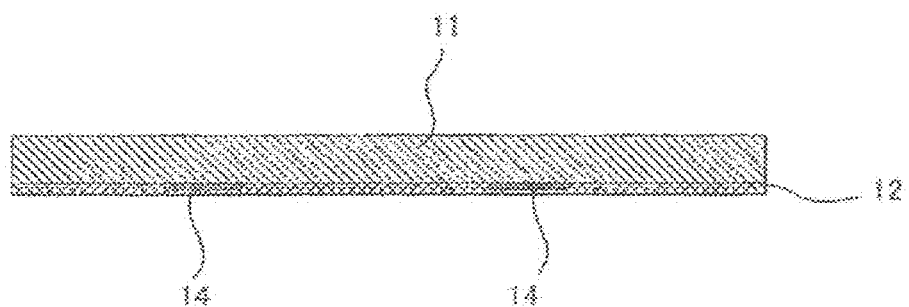
FIG. 8 shows a schematic cross-section of another example of the photocatalyst-containing layer-side basal plate of the present invention.
Figure 9:
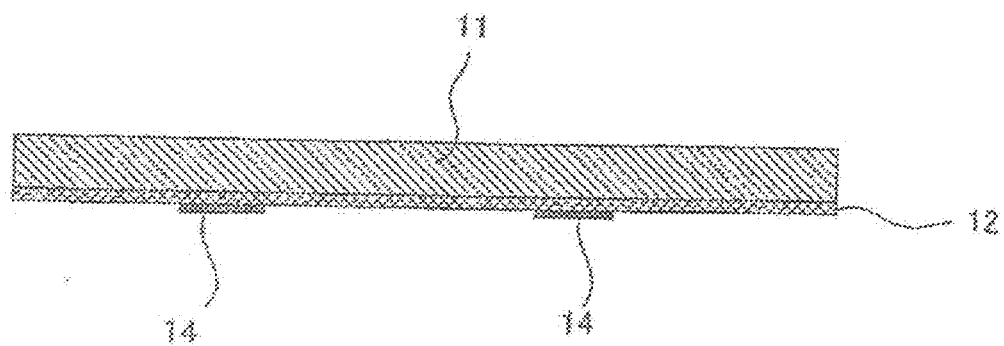
FIG. 9 shows a schematic cross-section of another example of the photocatalyst-containing layer-side basal plate of the present invention.

In one embodiment, as shown in FIG. 8, for example, a photocatalyst-containing layer-side light shielding part 14 is formed on a base body 11 and a photocatalyst-containing layer 12 is formed thereon such that a photocatalyst-containing layer-side basal plate is formed. In the other embodiment, as shown in FIG. 9, for example, a photocatalyst-containing layer 12 is formed on a base body 11 and a photocatalyst-containing layer-side light shielding part 14 is formed thereon such that a photocatalyst-containing layer-side basal plate is obtained.

In either embodiment, compared with the case where a photomask is used, it becomes possible to reduce the influence of energy scattering in the base body, for example. This is because the photocatalyst-containing layer-side light shielding part is placed in the vicinity of the position at which the photocatalyst-containing layer and the cell adhesiveness-variable material layer are placed. Thus, patterned energy irradiation can be carried out in a very accurate manner.

Further, in the embodiment where a photocatalyst-containing layer-side light shielding part is formed on the photocatalyst-containing layer, when the photocatalyst-containing layer and the cell adhesiveness-variable material layer are placed at a certain position, the film thickness of the photocatalyst-containing layer-side light shielding part is preferably set to be equivalent to the width of the gap therebetween. Thus, it is advantageous in that the photocatalyst-containing layer-side light shielding part can be used as a spacer with which the gap can be determined to have a certain width. In addition, if the height of such spacer is insufficient, another spacer may separately be formed on the light shielding part.

Specifically, when the photocatalyst-containing layer and the cell adhesiveness-variable material layer are placed with a certain gap therebetween such that they are opposed to each other, the photocatalyst-containing layer-side light shielding part and the cell adhesiveness-variable material layer are placed so as to come into close contact with each other. Thus, it becomes possible to provide a certain gap in an accurate manner. Then, energy irradiation is carried out from the side of the photocatalyst-containing layer-side basal plate in the aforementioned state. As a result, it becomes possible to form a cell adhesiveness-variation pattern on the cell adhesiveness-variable material layer with high precision.

Such method for forming a photocatalyst-containing layer-side light shielding part is not particularly limited. The method is adequately selected and used depending on properties of the formed surface of a photocatalyst-containing layer-side light shielding part, shielding properties of the light shielding part relative to required energy, and the like.

For instance, a photocatalyst-containing layer-side light shielding part may be formed in a manner such that a metal thin film made of chromium or the like having a thickness of about 1000 to 2000 Å is formed by a sputtering method, a vacuum evaporation method, or the like, followed by patterning. Examples of such patterning method that can be used include general patterning methods such as sputtering.

In addition, it is also possible to employ a method wherein a layer made of a resin binder containing light-shielding particles such as carbon fine particles, metallic oxides, inorganic pigments, and organic pigments is formed in a pattern. Examples of such resin binder used include a resin mixture of one or more members selected from a group consisting of polyimide resin, acryl resin, epoxy resin, polyacrylamide, polyvinyl alcohol, gelatin, casein, and cellulose. Also, photosensitive resin, oil-in-water emulsion-type resin compounds such as reactive silicone that has been emulsified, and the like can be used. The thickness of such resin-made light shielding part can be set to 0.5 to 10 μm. Examples of a method for patterning such resin light shielding part that can be used include methods such as a photolithography method and a printing method that are in general use.

Moreover, the above description regarding a position at which a photocatalyst-containing layer-side light shielding part is formed indicates a gap between the base body and the photocatalyst-containing layer and the surface of the photocatalyst-containing layer. In addition, a photocatalyst-containing layer-side light shielding part may be formed on the surface of a base body where the photocatalyst-containing layer is not formed. In such embodiment, it can be considered that a photomask, for example, is allowed to come into close contact with the surface in a detachable manner. Thus, such embodiment can be preferably applied to a case where a variety of cell adhesiveness-variation patterns are prepared in small lots.

d. Primer Layer

Next, the primer layer used in a photocatalyst-containing layer-side basal plate of this embodiment will be described. In this embodiment, a primer layer may be formed between a photocatalyst-containing layer-side light shielding part and a photocatalyst-containing layer in the aforementioned case where a photocatalyst-containing layer-side light shielding part is formed in a pattern on a base body and a photocatalyst-containing layer is formed thereon such that a photocatalyst-containing layer-side basal plate is obtained.

The action and function of such primer layer remains unclear. However, when a primer layer is formed between a photocatalyst-containing layer-side light shielding part and a photocatalyst-containing layer, such primer layer is considered to exert a function of preventing the dispersion of impurities such as metals and metal ions and the generation of impurities from openings that exist within a photocatalyst-containing layer-side light shielding part and among photocatalyst-containing layer-side light shielding parts. Such impurities cause inhibition of a change in cell adhesiveness of a cell adhesiveness-variable material layer due to photocatalytic action, and in particular, they are residues generated upon the patterning of a photocatalyst-containing layer-side light shielding part. Thus, when a primer layer is formed, a process of causing a change in cell adhesiveness proceeds at high sensitivity such that a high-resolution pattern can be obtained.

In addition, in this embodiment, a primer layer is intended to prevent impurities that exist in openings from affecting photocatalytic action; the openings are formed among photocatalyst-containing layer-side light shielding parts as well as within a photocatalyst-containing layer-side light shielding part. Thus, a primer layer is preferably formed on the entirety of the surface of a photocatalyst-containing layer-side light shielding part, including the opening.

The primer layer of this embodiment is not particularly limited as long as it is structured such that a photocatalyst-containing layer-side light shielding part of a photocatalyst-containing layer-side basal plate and a photocatalyst-containing layer do not come into contact with each other.

A material that constitutes such primer layer is not particularly limited; however, inorganic materials are preferred since they are unlikely to be degraded due to photocatalytic action. Specific examples thereof include amorphous silica. When amorphous silica is used, precursors of amorphous silica are silicon compounds represented by the following general formula: $SiX_4$ (where X is halogen, methoxy, ethoxy, or acetyl). Silanol, which is a hydrolysate of such silicon compound, or polysiloxane having an average molecular weight of not more than 3000 are preferable.

In addition, the film thickness of a primer layer is preferably 0.001 to 1 μm and particularly preferably 0.001 to 0.1 μm.

(2) Energy Irradiation

Next, the energy irradiation of this embodiment will be described. In this embodiment, the cell adhesiveness-variable material layer and the photocatalyst-containing layer of the photocatalyst-containing layer-side basal plate are placed such that they are opposed to each other. Then, energy irradiation is carried out from a certain direction such that a pattern in which cell adhesiveness of the cell adhesiveness-variable material layer is varied can be formed.

It has been determined that the aforementioned placement is to be carried out in a manner such that photocatalytic action substantially influences the surface of the cell adhesiveness-variable material layer. Thus, the photocatalyst-containing layer and the cell adhesiveness-variable material layer are placed such that they physically come into contact with each other, or there exists a certain gap therebetween. Such gap is preferably not more than 200 μm.

Considering a highly accurate pattern is obtained and a photocatalyst has good sensitivity, and improved efficiency in terms of a change in cell adhesiveness of a cell adhesiveness-variable material layer can be obtained, the gap is preferably 0.2 to 10 μm and particularly preferably 1 to 5 μm in this embodiment. Such range of gap is effectively applied to a cell adhesiveness-variable material layer having a small area that allows control of a gap with high accuracy.

Meanwhile, when a cell adhesiveness-variable material layer having a large area not less than 300×300 mm in size is subjected to treatment, it is very difficult to form a fine gap as described above between a photocatalyst-containing layer-side basal plate and a cell adhesiveness-variable material layer in a manner such that they do not come into contact with each other. Thus, when a cell adhesiveness-variable material layer has a relatively large area, the gap is preferably 10 to 100 μm and particularly preferably 10 to 20 μm. The gap within such range does not cause problems of pattern accuracy deterioration, such as a vaguely outlined pattern, or problems of efficiency deterioration with regard to a change in cell adhesiveness due to deterioration in sensitivity of a photocatalyst. Further, an effect that results in no occurrence of irregularity with regard to a change in cell adhesiveness of a cell adhesiveness-variable material layer can be obtained.

As described above, when a cell adhesiveness-variable material layer having a relatively large area is subjected to energy irradiation, a positioning device in an energy irradiation apparatus is set up in a manner such that the gap is set to be preferably 10 to 200 μm and particularly preferably 10 to 20 μm. With such range of set values, the pattern accuracy and the sensitivity of the photocatalyst do not significantly deteriorate. In addition, it becomes possible to place a photocatalyst-containing layer-side basal plate and a cell adhesiveness-variable material layer in a manner such that they do not come into contact with each other.

As described above, a photocatalyst-containing layer and the surface of a cell adhesiveness-variable material layer are placed with a certain gap therebetween such that a reactive oxygen species generated by oxygen, water, and photocatalytic action becomes detachable with ease. That is, when the gap between a photocatalyst-containing layer and a cell adhesiveness-variable material layer becomes smaller than the above range, the reactive oxygen species is unlikely to become detachable. As a result, the rate of change in cell adhesiveness might be decelerated, which is not preferred. In addition, when the gap becomes larger than the above range, the reactive oxygen species generated is unlikely to reach a cell adhesiveness-variable material layer. As a result, the rate of change in cell adhesiveness also might be decelerated, which is not preferred.

Examples of a method wherein a photocatalyst-containing layer and a cell adhesiveness-variable material layer are placed while such very narrow gap is uniformly formed therebetween include a method using a spacer. In such case, with the use of a spacer, the gap can be uniformly formed. In addition, at a position at which such spacer is sandwiched between a photocatalyst-containing layer and a cell adhesiveness-variable material layer, photocatalytic action does not affect the surface of the cell adhesiveness-variable material layer. Thus, when such spacer has a pattern similar to the aforementioned cell adhesiveness-variation pattern, it becomes possible to form a certain cell adhesiveness-variation pattern on a cell adhesiveness-variable material layer.

In this embodiment, such placement conditions may be maintained at least during energy irradiation.

Herein, the types of energy irradiated, energy irradiation methods, and the amount of energy irradiation are similar to those used in the first embodiment described above.

DESCRIPTION OF THE PREFERRED EMBODIMENTS

Hereafter, the present invention will be described in greater detail with reference to the following examples, although the technical scope of the present invention is not limited thereto.

(Example 1) Cell-Containing Sheet Made of an Amnion-Derived Support 1-1. Preparation of a Substrate for Cell Arrangement First, 1.5 g of fluoroalkylsilane TSL8233 (GE Toshiba Silicone Co., Ltd.), 5.0 g of tetra methoxysilane TSL8114 (GE Toshiba Silicone Co., Ltd.), and 2.4 g of $5.0 \times 10^{-3}$ NHCl were mixed together for 12 hours. The resultant was diluted 10-fold with isopropyl alcohol.

Next, 2.0 g of the resulting solution was applied to a polyester film substrate 10 cm×10 cm in size and 150 μm in thickness using a spin coater at 1000 rpm for 5 seconds. The substrate was dried at a temperature of 150° C. for 10 minutes.

Subsequently, 3.0 g of a titanium oxide sol solution (STK-03; Ishihara Sangyo Kaisha, Ltd.) that was diluted 3-fold with isopropyl alcohol was determined to be a composition for a photocatalyst-containing layer.

The composition for a photocatalyst-containing layer was applied to the pattern surface of a negative photomask (quartz) having a line-and-space pattern, on which 60 μm wide lines and 300 μm wide spaces are alternatively arranged, using a spin coater at 700 rpm for 3 seconds. The photomask was subjected to drying treatment at 150° C. for 10 minuets such that a photomask having a transparent photocatalyst-containing layer was created.

The photocatalyst-containing layer side of the photomask and the cell adhesiveness-variable material layer side of the aforementioned substrate were placed at a distance of 10 μm, followed by UV-exposure for a given time at an illuminance of 25.0 $mW/cm^2$ from the photomask side using a mercury lamp (wavelength: 365 nm). Thus, the substrate for cell arrangement was obtained, which has a cell adhesiveness-variation pattern on which 60 μm wide lines serving as cell adhesiveness promoted regions and 300 μm wide spaces serving as cell adhesiveness inhibited regions were alternatively arranged.

1-2. Preparation of an Amnion-Derived Support

Amnion was aseptically collected from a case in which there had been no complications in the mother or the fetus. With regard to the provision of appendages of the fetus, informed consent was previously obtained in accordance with the Declaration of Helsinki. The amnion was washed twice using sterilized PBS (phosphate buffered saline) supplemented with 1% Antibiotic-Antimycotic (GIBCO). The amnion was cut into a 2×3 cm size. The amnion was kept at −80° C. using a preservation solution containing DMEM and sterilized glycerol at a ratio of 1:1. The frozen amnion was thawed at 27° C. in a thermostatic bath at the time of use. Then, the amnion was washed three times with sterilized PBS and placed in a PBS solution supplemented with 0.02% EDTA, followed by incubation in a $CO_2$ incubator for 1 hour. Thereafter, the amnion was washed with sterilized PBS and chorion and thelium were removed therefrom using a cell scraper.

1-3. Cell Culture

As cultured cells, bovine carotid artery-derived vascular endothelial cells (Prostag Leukotress, vol. 62, 161, 2000) at $10^{th}$ to $19^{th}$ passages were used. The bovine carotid artery-derived vascular endothelial cells that grew to confluency in a 10-cm dish were removed from the dish by 0.05% trypsin/EDTA treatment. The cells in a floating state were subjected to cell membrane staining in such state using PKH Fluorescent Cell Linker Kits (PKH26 red/General Cell Membrane PKH26-GL, Sigma). The cell number was counted using a Coulter Counter™ ZM (Coulter Counter) such that the cell density was adjusted to $10^6$ cells/ml.

The substrate for cell arrangement prepared in 1-1 was sterilized using an autoclave. The substrate was placed in a cluture dish (well size of 76×26 mm (1976 mm$^2$); Heraeus Quadriperm™). The endothelial cells were diluted with a medium and seeded on the dish such that the cell density was adjusted to $10^6$ cells/5 ml per well. Then the cells were cultured in a $CO_2$ incubator for 16 hours. After patterned cell adhesion was confirmed, the culture supernatant was suctioned, and was replaced with a 0.3% bovine fetal serum-containing MEM medium, followed by shaking for 1 hour in the longitudinal direction of the cell pattern using a seesaw shaker (NISSIN).

1-4. Cell Transfer

On the amnion-derived support prepared in 1-2, the aforementioned substrate for cell arrangement on which the cell pattern had been formed was placed in a manner such that the cells and the amnion were allowed to come into contact with each other. The support with the substrate was kept in a clean bench for 2 minutes. Then, 5 ml of a cluture solution (0.3% bovine fetal serum-containing MEM medium) was added thereto, followed by culture for 24 hours.

After lumen formation of the bovine vascular endothelial cells was confirmed, the substrate was removed. Thus, a cell-containing sheet on which the luminal pattern of bovine vascular endothelial cells was formed on the amnion was obtained. The line width of the luminal pattern was about 25 to 35 μm.

1-5. Implantation

A BALB/c nude mouse (6 weeks old) was anesthetized with Nembutal at a dose of 30 μg/kg. The following implant operation was aseptically performed.

The abdomen of the mouse was disinfected with povidone-iodine (trade name: isodine). Skin flap incision was made on the abdominal skin (epidermis, corium, and subcutaneous tissue) in a downward direction. The subcutaneous tissue was removed by curettage using a MICRO curette (F. S. T) such that the skin was made thinner. Then, the amnion to which endothelial cells had been transferred was subcutaneously implanted. The incision was sutured with 4-0 silk (Nesco suture) and the sutured area was disinfected with isodine. Thereafter, the mouse was raised in a sterilized cage for 7 days.

After being raised, the mouse was euthanized with ether. Immediately thereafter, the tissue between the implant site and peritoneum was picked out. Then, the tissue was embedded in a frozen OCT compound. Frozen sections were prepared using a microtome (JUNG FRIGOT, Leica). The sections were fixed with 4% PFA for inclusion. Some sections were HE-stained.

1-6. Results

Figure 10:
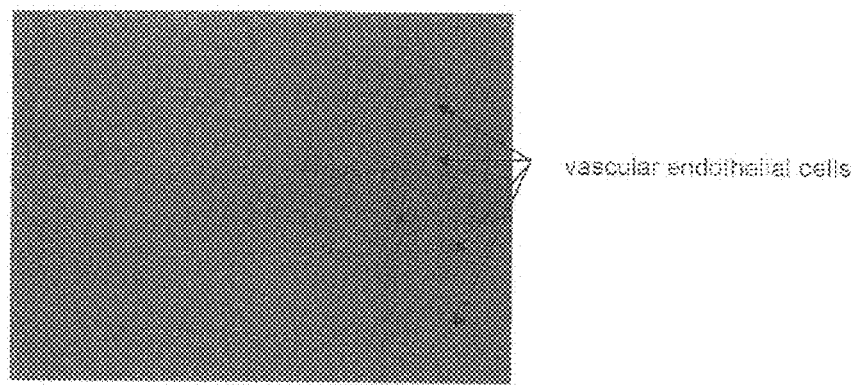
FIG. 10 shows a picture of the cell-containing sheet of the present invention.
Figure 11:
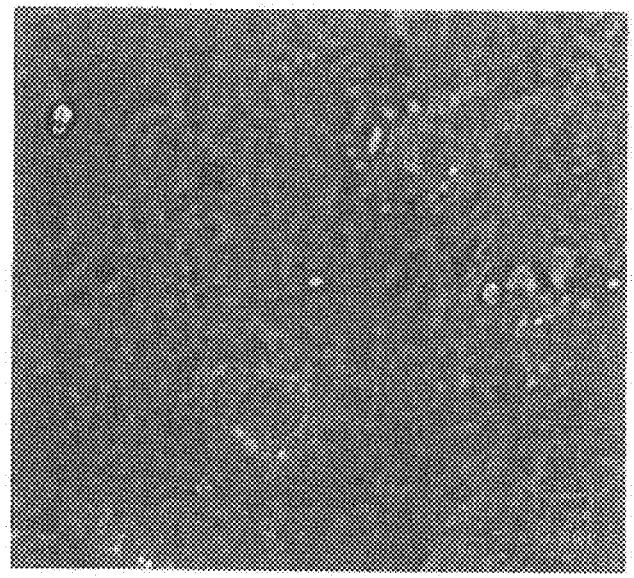
FIG. 11 shows a fluorescence microscopic image of the cell-containing sheet of the present invention.

Lumen formation of the endothelial cells on the amnion was microscopically observed (FIGS. 10 and 11). In addition, as a result of observation of the sections prepared from the sample picked out from the raised mouse using a laser microscope (LSM510META, Carl Zeiss), lumen formation of the cells stained red with PKH26 red was confirmed (FIG. 11). The results indicated that the implanted lumen tissue was preserved without experiencing collapse after implantation. Moreover, hemocytes were found in blood vessels of HE-stained sections, indicating that the implanted lumen tissue had a bloodstream.

(Example 2) Cell-Containing Sheet Made of a Support Obtained by Applying Collagen to a Biodegradable Polymer Material As with the case of Example 1, a cell-containing sheet was prepared except that a support in which collagen had adhered to polylactic acid film was used. The support was prepared by coating a polylactic acid film with swine-derived collagen for tissue culture (Cellmatrix TypeI-A, Nitta Gelatin). Accordingly, the cell-containing sheet was obtained, in which the luminal pattern of vascular endothelial cells was formed on the collagen layer supported by the polylactic acid film.

The cell-containing sheet of the present invention is available as a starting material for various types of medical materials such as artificial organs, wound-covering materials, wound-filling materials, and wound-healing materials.

(Example 3) Availability in a Hindlimb Ischemia Model

As cultured cells, bovine carotid artery-derived vascular endothelial cells (Prostag Leukotress, vol. 62, 161, 2000) at $10^{th}$ to $19^{th}$ passages were used. Bovine carotid artery-derived vascular endothelial cells that grew to confluency in a 10-cm dish were removed from the dish by 0.05% trypsin/EDTA treatment. The cells in a floating state were subjected to cell membrane staining using PKH Fluorescent Cell Linker Kits (PKH26 red/General Cell Membrane PKH26-GL, Sigma). The cell number was counted using a hemocytometer such that the cell density was adjusted to $10^6$ cells/ml.

The substrate for cell arrangement prepared in 1-1 was sterilized using an autoclave. The substrate was placed in a culture dish (well size of 76×26 mm (1976 mm$^2$); Heraeus Quadriperm™). The endothelial cells were diluted with a medium and seeded on the dish such that the cell density was adjusted to $10^6$ cells/5 ml per well. The cells were cultured in a $CO_2$ incubator for 16 hours. After patterned cell adhesion was confirmed, the culture supernatant was suctioned, and replaced with a 0.3% bovine fetal serum-containing MEM medium, followed by shaking for 1 hour in the longitudinal direction of the cell pattern using a seesaw shaker (NISSIN).

On the amnion-derived support prepared in Example 1-2, the aforementioned substrate for cell arrangement on which the cell pattern had been formed was placed in a manner such that the cells and the amnion were allowed to come into contact with each other. The support with the substrate was kept in a clean bench for 30 seconds. Then, 2 ml of a cluture solution (0.3% bovine fetal serum-containing MEM medium) was added thereto, followed by culture for 24 hours.

After lumen formation of the bovine vascular endothelial cells was confirmed, the substrate w as removed. Thus, a cell-containing sheet on which the luminal pattern of bovine vascular endothelial cells was formed on the amnion was obtained. The line width of the luminal pattern was about 25 to 35 μm.

A BALB/c nude mouse (6 weeks old) was anesthetized with Nembutal at a dose of 50 μg/kg. The following implant operation was aseptically performed.

The right hindlimb and the surface of the abdomen of the mouse were disinfected with isodine. The skin (epidermis, corium, and subcutaneous tissue) on the inguinal region was incised in a T shape. The inguinal ligament was dissected out and the femoral artery was ligated using 9-0 virgin silk (Mani, Inc.), followed by cutting the artery at the peripheral side. Ligation of the saphenous artery was performed at the knee level on the peripheral side in a similar manner, followed by cutting the artery at the body side. All vessel branches between both ligations (and cut edges) were separated and arteries were removed. During each process, all nerves and veins running parallel were carefully separated without damage.

The above cell-containing sheet was cut into a 4×7 mm size. The sheet was implanted into the area from which the artery had been removed so as to be fixed to the fascia using 7-0 virgin silk (Mani, Inc.). After single ligation using 7-0 virgin silk (Mani, Inc.) was carried out and the incision was sutured, the sutured area was disinfected with isodine. Thereafter, the mouse was raised in a sterilized cage for 7 days.

Figure 12:
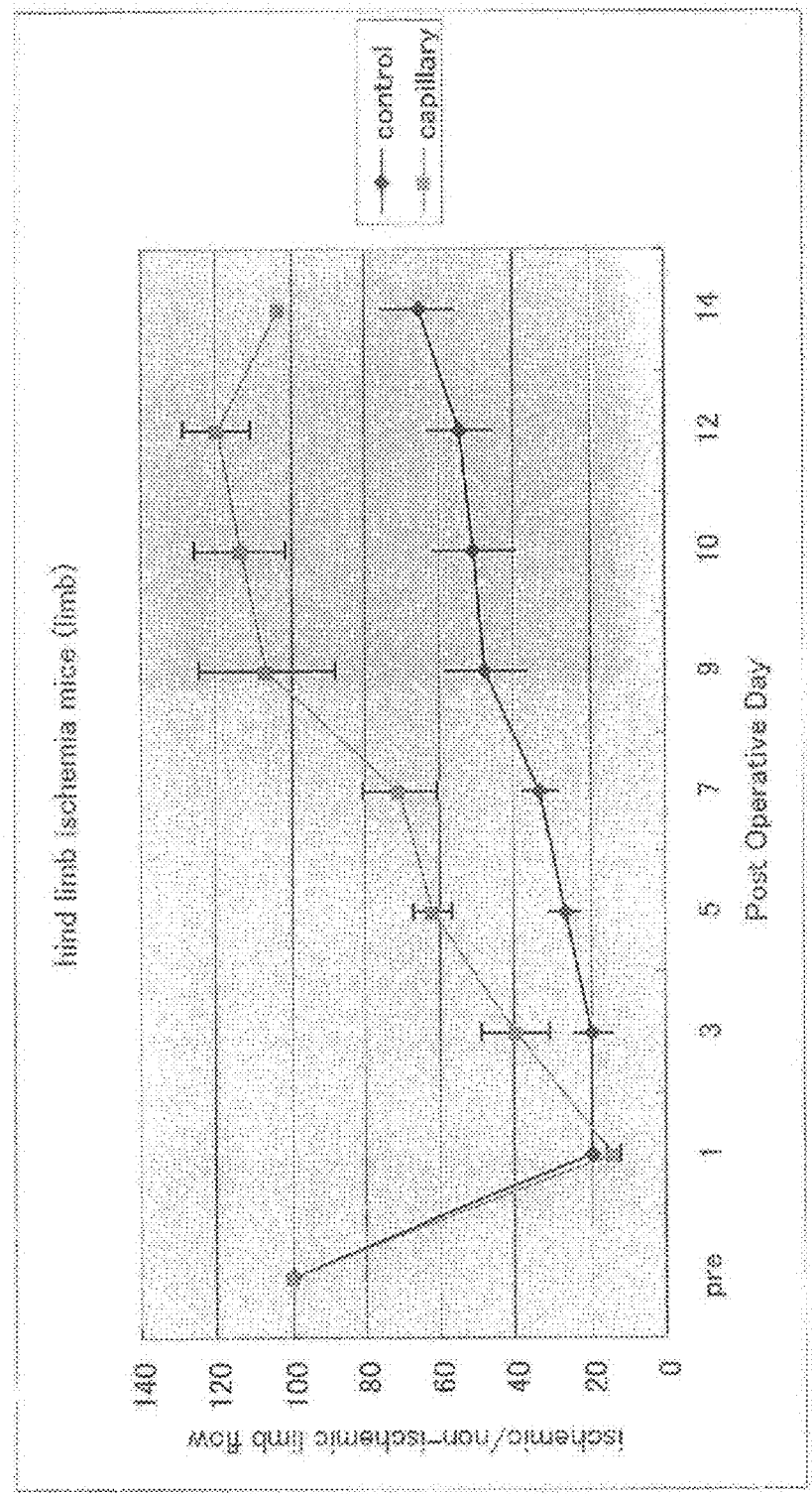
FIG. 12 shows results of a comparison between the recovery in the bloodstream of the affected limb (operated side) relative to the bloodstream of the unaffected limb (unoperated side) in a murine hindlimb ischemia model (capillary) into which a cell-containing sheet had been implanted and in the murine hindlimb ischemia model (control) into which a non-cell-containing sheet (amnion-derived support only) had been implanted. The figure shows that the recovery in bloodstream in the mouse into which the cell-containing sheet had been implanted was significantly better than that in the control case.
Figure 13:
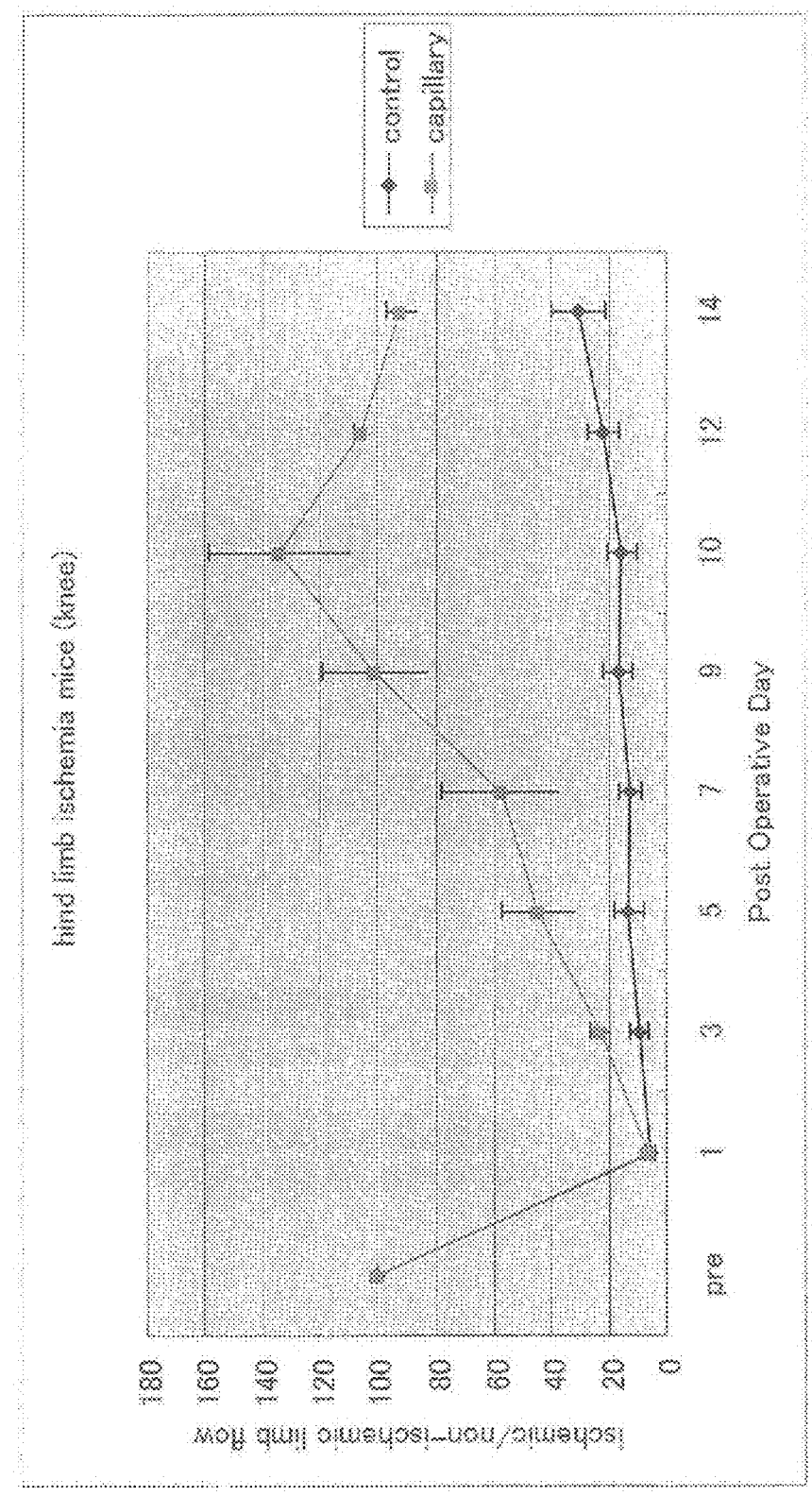
FIG. 13 shows results of a comparison between the recovery in the bloodstream of the affected limb (operated side) relative to the bloodstream of the unaffected limb (unoperated side) in a murine hindlimb ischemia model (capillary) into which a cell-containing sheet had been implanted and in the murine hindlimb ischemia model (control) into which a non-cell-containing sheet (amnion-derived support only) had been implanted. The figure shows that the recovery in the bloodstream in the mouse into which the cell-containing sheet had been implanted was significantly better than that in the control case.
Figure 14:
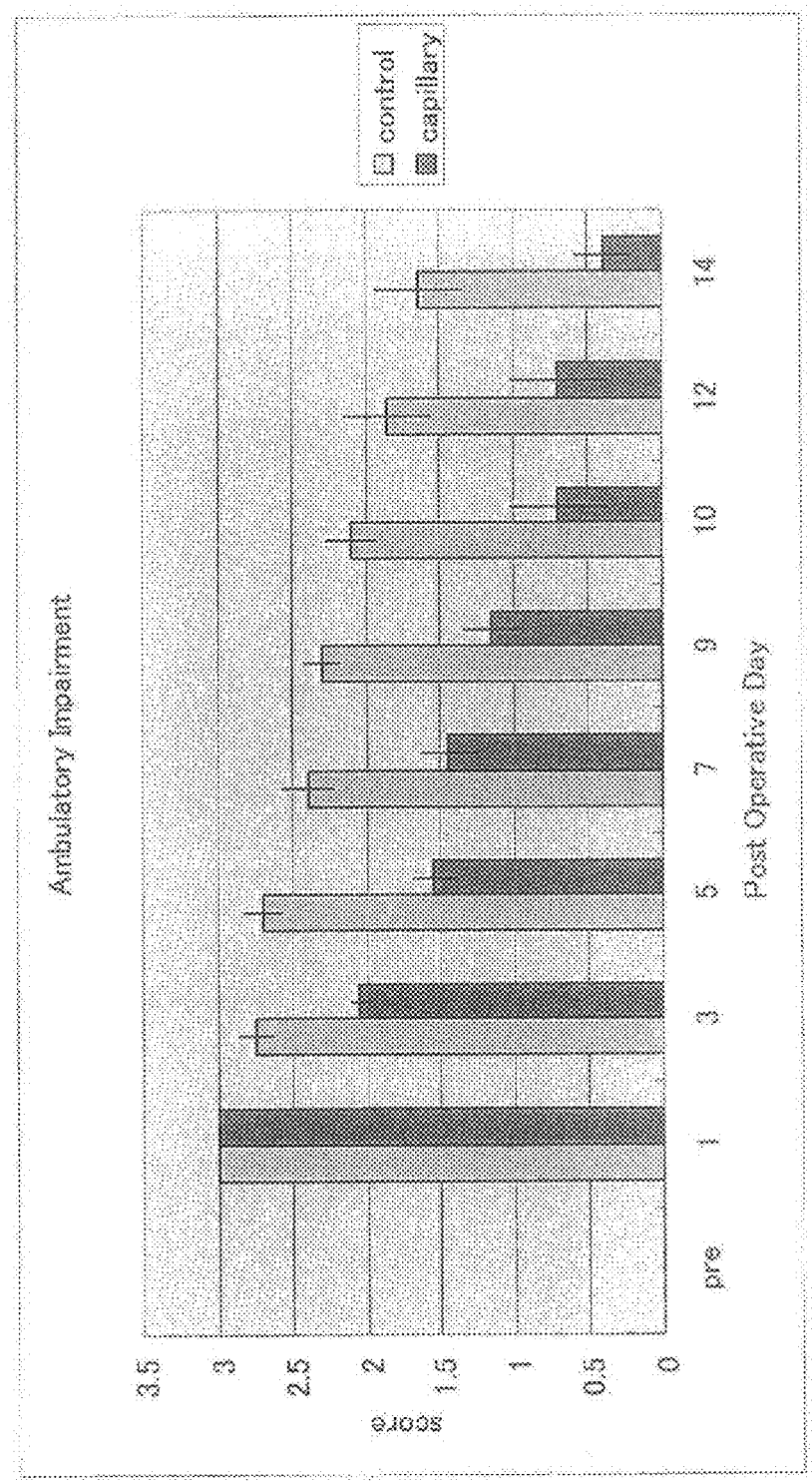
FIG. 14 shows results of a comparison between clinical scores of a murine hindlimb ischemia model (capillary) into which a cell-containing sheet had been implanted and those of a murine hindlimb ischemia model (control) into a which non-cell-containing sheet (amnion-derived support only) had been implanted. The figure shows that clinical scores of the mouse into which the cell-containing sheet had been implanted were quickly improved.

A mouse with hindlimb ischemia into which a non-cell-containing sheet had been implanted (the amnion-derived support prepared in Example 1 only) was designated as a negative control with respect to the above mouse with hindlimb ischemia into which a cell-containing sheet had been implanted. The bloodstreams of both hindlimbs of each mouse were measured using a laser Doppler bloodstream imager (moor LDI: MOOR) before operation and on postoperative days 1, 3, 5, 7, 9, 12, and 14. The results were subjected to quantitative analysis. The recovery in the bloodstream of the affected limb (operated side) relative to the bloodstream of the unaffected limb (unoperated side) in each mouse was observed. As a result, it was confirmed that the recovery in the bloodstream of the hindlimb and that of the crus in the mouse into which the cell-containing sheet had been implanted were significantly better than those in the control case (FIGS. 12 and 13). In addition, it was confirmed that clinical scores (Circulation, Volume 113, 118-124, 2006) of the mouse into which the cell-containing sheet had been implanted were quickly improved (FIG. 14). These results indicate that implanted lumens improve the recovery rate of bloodstream in a murine hindlimb ischemia model.

Statistical analysis was conducted by a Student's t-test where the significant difference was determined to be at $P<0.01$.

(Example 4) Human Periodontal Ligament-Derived Cell-Containing Sheet Made of an Amnion-Derived Support 4-1. Preparation of Substrate for Cell Arrangement Fluoroalkylsilane XC98-B2472 (GE Toshiba Silicone Co., Ltd.) was diluted 10-fold with isopropyl alcohol and subjected to filtration through a 0.45-μm membrane filter.

Next, 2.0 g of the resulting solution was applied to a glass substrate 10 cm×10 cm in size and 700 μm in thickness using a spin coater at 1000 rpm for 5 seconds. The obtained substrate was dried at a temperature of 150° C. for 10 minutes.

The composition for a photocatalyst-containing layer used in Example 1 was applied to the pattern surface of a quartz photomask, on which a number of 400 μm$^2$ light transmission areas were arranged at 400 μm intervals, using a spin coater at 700 rpm for 3 seconds. The photomask was subjected to drying treatment at 150° C. for 10 minuets such that a photomask having a transparent photocatalyst-containing layer was created.

The photocatalyst-containing layer side of the photomask was slowly placed on the cell adhesiveness-variable material layer side of the aforementioned substrate, followed by UV exposure for a given time at an illuminance of 25.0 mW/cm$^2$ from the photomask side using a mercury lamp (wavelength: 365 nm). Thus, the substrate for cell arrangement having a cell adhesiveness-variation pattern in which 400 μm$^2$ cell adhesiveness promoted regions were arranged at 400 μm intervals was obtained.

4-2. Cell Culture

As cultured cells, human periodontal ligament cells were used. Cells grown on human periodontal ligament were collected. The collected cells were stained with PKH26. The cells were diluted with a 20% bovine fetal serum-containing DMEM medium and seeded on a culture dish in a manner such that a single substrate for cell arrangement contained $8\times10^4$ cells. The cells were cultured in a incubator ($CO_2$, 37° C.) for 24 hours.

4-3. Cell Transfer and Culture

On the amnion-derived support prepared in Example 1-2, the substrate for cell arrangement to which the cells adhered was placed in a manner such that the cells and the amnion were allowed to come into contact with each other. The support with the substrate was kept in a clean bench for 2 minutes. Then, 5 ml of a 20% bovine fetal serum-containing MEM medium was added thereto, followed by culture for 24 hours. Thereafter, the substrate was removed. Thus, a cell-containing sheet in which a pattern of human periodontal ligament cells was formed on the amnion was obtained.

4-4. Implantation

A nude rat (male, 4 weeks old) was purchased. The rat was raised for 1 week under the environment of an animal breeding facility of a laboratory. The animal was anesthetized via ether inhalation and subjected to body weighing. The animal was peritoneally anesthetized with pentobarbital s odium (trade name: Nembutal) in a dose of 50 mg/kg. The anesthetic depth was maintained via ether inhalation. The parietal bone of the animal was exposed under anesthesia. The parietal bone was incised using a No. 15c scalpel and removed by curettage using a curette such that a 2 mm$^2$ periosteum-deficient area was prepared. After hemostasis was achieved, the periosteum-deficient area was covered with saline-containing gauze so as to prevent dehydration of the area. The cell-containing sheet prepared in 4-3, on which the pattern of human periodontal ligament cells had been formed, was cut into a 2.5 mm$^2$. The square sheet was placed on the periosteum-deficient area such that the cells were allowed to come into contact with the bone surface, followed by suturing using a 10-0 nylon suture for fixation.

Results

A week after implantation, observation using a stereoscopic microscope revealed that clinically successful curing had been achieved in the control group (with the amnion sheet only) and the experimental group (with the cell-containing sheet on which the pattern of human periodontal ligament cells had been formed). In the case of the experimental group, as compared with the control group, blood vessel induction from the neighboring tissue to the implanted area was macroscopically confirmed at a significant level. In addition, PKH-positive cells that were apparently in contact with the bone surface were microscopically observed. Further, some lumens were found to be composed of several PKH-positive cells and they were positive for CD31, which is an endothelial cell marker.

These results suggest that capillaries were regenerated not only via blood vessel induction from the neighboring tissue to the implanted area but also from the implanted periodontal ligament-derived cells.

(Example 5) Cell-Containing Sheet Made of a Support in which Matrigel was Applied to a Collagen Film As with the case of Example 1, a cell-containing sheet was prepared except that a support in which Matrigel (Becton, Dickinson and Company) was applied to a collagen film was used. Accordingly, a cell-containing sheet was obtained in which the luminal pattern of vascular endothelial cells was formed on Matrigel supported by a collagen film.

All publications, patents, and patent applications cited herein are incorporated herein by reference in their entirety.

What is claimed is:

1. A method for forming tissue in a mammal, said method comprising fixedly implanting a cell-containing sheet into the body of a mammal by suturing said cell-containing sheet into the body of said mammal, and allowing said tissue to form,
    wherein said cell-containing sheet comprises cells and a support comprising a bioabsorbable material, wherein said support has a cell-adhesion protein-containing layer on the surface thereof, wherein said cells are arranged in a pattern on the cell-adhesion protein-containing layer, and wherein said support comprises an amnion consisting of stratum compactum and basal lamina, and
    wherein the implanting comprises allowing a side of the cell-containing sheet on which the cells are arranged thereon to come into contact with an implant site of the body of said mammal.

2. The method of claim 1, wherein said cells comprise vascular endothelial cells, and the tissue formed comprises vascular tissue.

3. The method of claim 1, wherein said cells comprise periodontal ligament cells, and the tissue formed comprises periodontal ligament.

4. A method of treating a disease in a mammal, said method comprising fixedly implanting a cell-containing sheet into the body of a mammal in need of such treatment by suturing said cell-containing sheet into the body of said mammal, and allowing said tissue to form,
    wherein said cell-containing sheet comprises cells and a support comprising a bioabsorbable material, wherein said support has a cell-adhesion protein-containing layer on the surface thereof, wherein said cells are arranged in a pattern on the cell-adhesion protein-containing layer, and wherein said support comprises an amnion consisting of stratum compactum and basal lamina, and
    wherein the implanting comprises allowing a side of the cell-containing sheet on which the cells are arranged thereon to come into contact with an implant site of the body of said mammal.

5. The method of claim 4, wherein said cells comprise periodontal ligament cells, and said disease is an oral disease.

6. The method of claim 4, wherein said cells comprise vascular endothelial cells, and said disease is an ischemic disease.

* * * * *